United States Patent
Nagino et al.

(10) Patent No.: US 9,823,197 B2
(45) Date of Patent: Nov. 21, 2017

(54) DETECTING METHOD, MICROARRAY ANALYZING METHOD, AND FLUORESCENCE READING DEVICE

(71) Applicant: Toray Industries, Inc., Tokyo (JP)

(72) Inventors: Kunihisa Nagino, Kamakura (JP); Syunpei Yoshikawa, Kamakura (JP)

(73) Assignee: Toray Industries, Inc. (JP)

( * ) Notice: Subject to any disclaimer, the term of this patent is extended or adjusted under 35 U.S.C. 154(b) by 264 days.

(21) Appl. No.: 14/433,972

(22) PCT Filed: Oct. 4, 2013

(86) PCT No.: PCT/JP2013/077159
§ 371 (c)(1),
(2) Date: Apr. 7, 2015

(87) PCT Pub. No.: WO2014/057893
PCT Pub. Date: Apr. 17, 2014

(65) Prior Publication Data
US 2015/0276604 A1    Oct. 1, 2015

(30) Foreign Application Priority Data
Oct. 12, 2012    (JP) .................................. 2012-227302

(51) Int. Cl.
*G01N 33/48*    (2006.01)
*G01N 33/50*    (2006.01)
(Continued)

(52) U.S. Cl.
CPC ..... *G01N 21/6486* (2013.01); *G01N 21/6452* (2013.01); *G01N 21/6456* (2013.01);
(Continued)

(58) Field of Classification Search
None
See application file for complete search history.

(56) References Cited

U.S. PATENT DOCUMENTS

2003/0152255 A1    8/2003    Kira et al.
2003/0152256 A1    8/2003    Kira et al.
(Continued)

FOREIGN PATENT DOCUMENTS

| | | |
|---|---|---|
| CN | 1657873 | 8/2005 |
| JP | 2003-148925 | 5/2003 |

(Continued)

OTHER PUBLICATIONS

English machine translation of WO 2012/101943 obtained on Feb. 28, 2017.*

(Continued)

*Primary Examiner* — Russell S Negin
(74) *Attorney, Agent, or Firm* — DLA Piper LLP (US)

(57) ABSTRACT

A detecting method includes irradiating a substrate having a concave and convex shape, with laser light collected by a lens; and detecting a height difference of the concave and convex shape by acquiring light intensity of reflected light and/or scattered light from the substrate as image data, and a light irradiation surface of the substrate is arranged at a position closer to the lens than a focal position of the lens is, reflected light and/or scattered light from the light irradiation surface is received as detected light, and a height difference of the substrate is detected based on a change in intensity of the received light.

9 Claims, 25 Drawing Sheets

(51) Int. Cl.
*G01N 21/64* (2006.01)
*G06F 17/10* (2006.01)

(52) U.S. Cl.
CPC ..... *G06F 17/10* (2013.01); *G01N 2021/6441* (2013.01); *G01N 2201/0461* (2013.01)

(56) References Cited

U.S. PATENT DOCUMENTS

| | | |
|---|---|---|
| 2007/0037155 A1 | 2/2007 | Tashiro et al. |
| 2010/0208061 A1 | 8/2010 | Lee et al. |
| 2013/0303403 A1 | 11/2013 | Ozaki et al. |

FOREIGN PATENT DOCUMENTS

| | | |
|---|---|---|
| JP | 2005-24532 | 1/2005 |
| JP | 2005-49282 | 2/2005 |
| JP | 2005-172840 | 6/2005 |
| JP | 2013-224894 | 10/2013 |
| WO | 2012/101943 | 8/2012 |

OTHER PUBLICATIONS

English machine translation of JP 2003148925 obtained on Mar. 1, 2017.*
The First Office Action dated Oct. 24, 2016, of corresponding Chinese Application No. 201380052862.2, along with an English translation.
Supplementary European Search Report dated May 10, 2016 of corresponding European Application No. 13845775.9.

\* cited by examiner

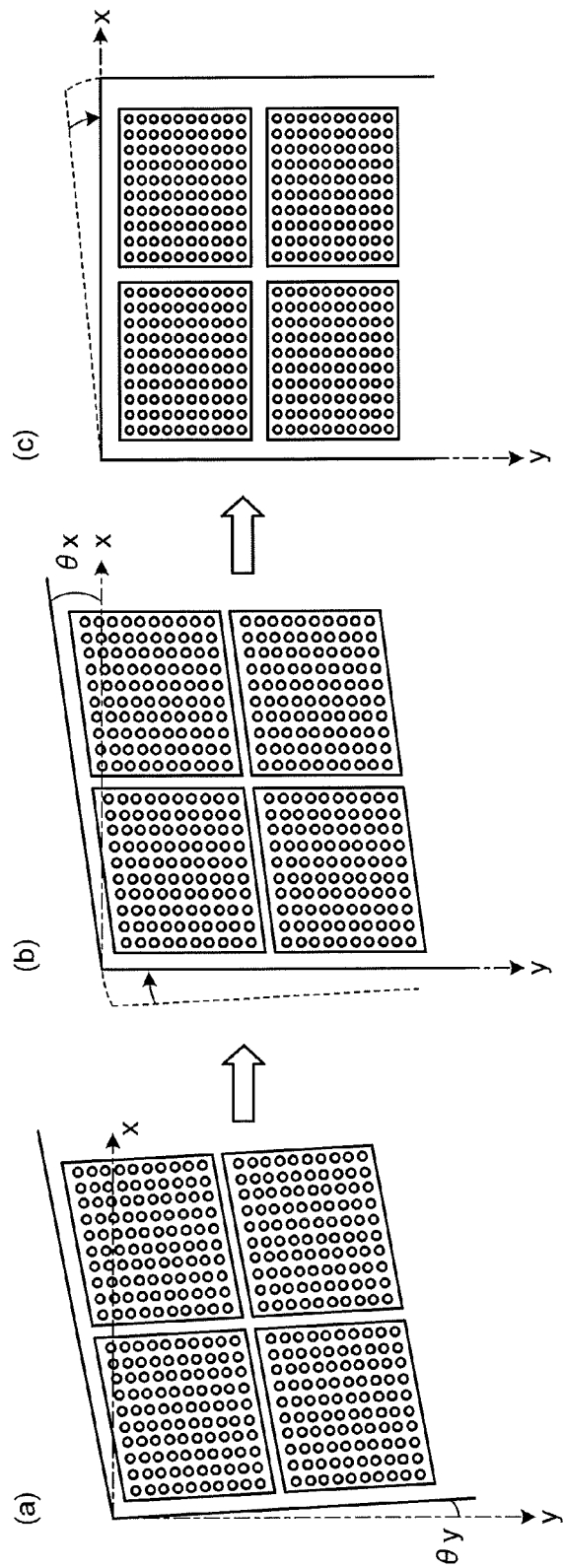

DETECTING METHOD, MICROARRAY ANALYZING METHOD, AND FLUORESCENCE READING DEVICE

TECHNICAL FIELD

This disclosure relates to a method of detecting a height difference of a concave and convex shape on a surface of a microarray, a microarray analyzing method, and a fluorescence reading device.

BACKGROUND

Since 1990, technology called microarray has started to be developed and used in the biological, medical, and pharmaceutical fields. A microarray is obtained by immobilizing several tens to several tens of thousands of probes onto a substrate made of glass, plastic, or the like, and is for detecting, with fluorescence or the like, by applying a sample (target) labeled with fluorescent molecules or the like to this substrate, binding reaction between the probes and the sample. Microarrays enable comprehensive measurement at one time and are expected to become essential to personalized medicine in the future.

Conventionally, a DNA microarray (hereinafter, "DNA chip") obtained by immobilizing DNAs as probes onto a substrate, a protein microarray obtained by immobilizing proteins as probes onto a substrate, a tissue microarray obtained by immobilizing a number of small specimens as probes onto a substrate, a compound microarray obtained by immobilizing a number of low-molecular compounds as probes onto a substrate, and the like, have been known.

Among them, the DNA chip has been put into practical use at the most advanced level, studies have been performed actively to search for genes related to diseases and perform examination and diagnosis by using those genes, and some of these have been put into practical use.

The DNA chip, which is one mode of a microarray, will be described in detail below.

The DNA chip is obtained by spotting (immobilizing), in a grid form, DNAs onto a substrate made of glass, resin, or the like. On the DNA chip, single stranded DNAs (DNA probes) are spotted as probes that are able to specifically react with a DNA sample to be labeled. The DNA probes to be used are those with known sequences. An optically detectable luminescent or fluorescent mark is added to the DNA sample (single stranded DNA) to be analyzed, the DNA sample having an unknown sequence. As a result, when the DNA sample with the unknown sequence to be analyzed is caused to flow onto the DNA chip, if the sequence of the DNA sample is in a complementary relation with a sequence of a DNA probe, the DNA probe and the DNA sample bond to each other to form a double stranded DNA. Therefore, when all of the DNA sample that has not bonded to any of the DNA probes is washed out, the DNA sample to be determined that remain on the DNA chip is made luminescent, and this luminescence is read by a reading device (scanner), the state of any double stranded DNAs is able to be observed as an image. That is, by analyzing distribution of luminescent marks on the DNA chip, presence of the gene to be sought for, whether or not a certain gene has been expressed, or the degree of the expression is able to be analyzed. As described above, by forming a DNA probe set having known sequences on a DNA chip and mounting the DNA probes having different sequences from one another on the DNA chip, genetic alteration, an expression amount of a gene, and the like are able to be detected.

FIG. 13 illustrates a series of procedural steps of DNA chip analysis in detail.

In a preprocessing step illustrated in FIG. 13, unknown DNAs contained in a DNA sample extracted from a specimen are amplified and a fluorescent mark (for example, Cy3, Cy5, or the like) is added to the DNAs (Step S201).

Next, in a hybridization step, the DNA sample added with the fluorescent mark is dropped onto a substrate of a DNA chip mounted with a number of types of DNA probes. The DNA sample bonds to the spotted DNA probe to form a double strand if the DNA sample is in a complementary relation with the spotted DNA probe (Step S202).

Next, in a washing step, the hybridized DNA chip is washed with a predetermined washer fluid (Step S203). Thereby, all of the DNA sample that has not bonded to the DNA probes arranged in a grid form is washed out.

Subsequently, the washed DNA chip is scanned by irradiation with light (Step S204). In the scanning step, the DNA chip is irradiated with laser light having a wavelength suitable to excite the fluorescent mark and fluorescence from the DNA sample bonded (hybridized) to the respective DNA probes is acquired as electric signals. Thereby, amounts of luminescence of the fluorescent mark added to the DNA sample bonded to the respective spotted DNA probes (genes) are measured and fluorescence image data, on which an analyzing process is to be performed based on the amounts of luminescence, are acquired.

In an analyzing step, a fluorescence intensity of each spot is calculated by using a template for the acquired fluorescence image data and various types of analyses are executed (Step S205).

FIG. 14 illustrates an example of a DNA chip 100 to be used in DNA chip analysis. The DNA chip 100 illustrated in FIG. 14 has a rectangular plate-like form having a concave and convex shape. The DNA chip 100 has a plurality of blocks 101 formed by a plate face thereof being divided in a grid form. On each of the blocks 101, a plurality of spots 102 are formed, which are each provided in an approximately column shape or truncated cone shape, immobilize DNA probes corresponding to individual genes, and are arrayed, with a predetermined number thereof in a row direction and a predetermined number thereof in a column direction, in a matrix form. Further, the plurality of blocks 101 are formed on a bottom portion of a concave portion 103 that has been notched into a rectangular column shape. The DNA probes arranged on the spots 102 correspond to genes, which have base sequences that have been already decoded and which are different from one another, and their arrangement positions on the block 101 are determined beforehand.

Further, FIG. 15 illustrates an example of a template to be applied to fluorescence image data of a DNA chip. As illustrated in FIG. 15, the template is divided into a plurality of (for example, 32 in FIG. 15) blocks (corresponding to the blocks 101), and detection areas (corresponding to the individual spots 102 of the DNA chip 100) that are arranged in a matrix form of "m" rows and "n" columns ("22×22" in FIG. 15) are provided on each block.

In the above-mentioned analyzing step, the detection areas on the template provided by an analysis tool are assigned to the individual spots 102 in the read fluorescence image data of the DNA chip (alignment) to calculate fluorescence intensities of the respective spots 102 in the corresponding detection areas. In that case, to execute the analysis accurately, an alignment process needs to be executed accurately such that the individual detection areas of the template are set correctly to the individual spots 102 on the image.

Methods of that alignment include a pattern matching method and a projection method in which alignment is made block by block. Like the technique disclosed in Japanese Laid-open Patent Publication No. 2005-172840, attempts to perform alignment accurately have been made, by using a chip spotted with a fluorescent substance called positive control or with a house-keeping gene contained in any specimen.

Furthermore, like the technique disclosed in Japanese Laid-open Patent Publication No. 2005-024532, a method has been devised, which performs alignment from an image acquired by making an image of a concave and convex shape from reflected light and/or scattered light from a substrate.

However, with any of the typical pattern matching method and projection method in which alignment is made block by block, accurate alignment is unable to be made unless an amount of hybridized sample DNA is large and the spots 102 that emit fluorescence of a sufficient intensity are present by a quarter to approximately a half of the spots 102 on each block 101. Thus, if a sample extracted from a specimen contains a small amount of DNAs, alignment may be unable to be performed accurately in some cases.

In contrast, the method of arranging a fluorescent substance by spotting the fluorescent substance has an advantage that alignment is able to be performed even if spots that emit fluorescence having a sufficient intensity are few, but has problems in that the number of DNAs that are able to be arranged on the spots 102 is reduced and the cost upon manufacturing the chips is increased, for example. Further, when the fluorescent substance is spotted, there is a risk that the fluorescent substance may liberate during the hybridization to contaminate the periphery of the positive control and data may not be able to be acquired.

It could therefore be helpful to provide a detecting method, a microarray analyzing method, and a fluorescence reading device that enable acquirement of an image, from which a height difference of a substrate is accurately detectable.

SUMMARY

We thus provide:

A detecting method including irradiating a substrate having a concave and convex shape, with laser light collected by a lens; and detecting a height difference of the concave and convex shape by acquiring light intensity of reflected light and/or scattered light from the substrate as image data, a light irradiation surface of the substrate is arranged at a position closer to the lens than a focal position of the lens is, reflected light and/or scattered light from the light irradiation surface is received as detected light, and a height difference of the substrate is detected based on a change in intensity of the received light.

An optical system that separates, from the detected light, regularly reflected light coming from the light irradiation surface, is used, at a time the light irradiation surface of the substrate is arranged at the focal position.

The light irradiation surface of the substrate is arranged at a position corresponding to "α" that is set such that "α/f" is in a predetermined range, where "f" is a focal length of the lens and "α" is a distance by which the substrate is brought closer to the lens from the focal position.

A microarray analyzing method irradiates a microarray, on which a concave and convex shape is formed and a plurality of probes that are able to bond to samples that are each fluorescence-labeled are arranged, with light including an excitation wavelength for the fluorescent label, via an objective lens, receives light from the microarray, and analyzes the microarray based on an image that is based on the received light. The microarray analyzing method includes: a fluorescence image data acquiring step of acquiring fluorescence image data by detecting fluorescence from the fluorescent label; an alignment image data acquiring step of acquiring, by detecting light from a surface of the microarray, alignment image data for performing alignment of the fluorescence image data; a detecting step of detecting, based on a change in light intensity in the alignment image data, a height difference of the concave and convex shape; a correcting step of correcting, based on the height difference of the concave and convex shape detected by the detecting step, the fluorescence image data; and a position determining step of determining a position of each probe in the fluorescence image data corrected by the correcting step, and in the alignment image data acquiring step, the alignment image data are acquired in a state where the surface of the microarray is arranged at a position close to the objective lens with respect to a focal position of the objective lens.

In the detecting step, from the alignment image data, three or more reference points are detected based on the change in light intensity, and in the correcting step, strain of the fluorescence image data is corrected based on the detected reference points.

In the correcting step, inclination angles θx and θy of the alignment image data based on the reference points are acquired, and strain of shear deformation of the fluorescence image data is corrected based on the inclination angles θx and θy and Equations (1) and (2) below.

$$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix} \quad (1)$$

$$\theta xy = \theta x - \theta y \quad (2)$$

In the alignment image data acquiring step, the alignment image data area acquired by arranging the surface of the microarray at a position corresponding to "α" that is set such that "α/f" is in a predetermined range, where "f" is a focal length of the objective lens and "α" is a distance by which the microarray is brought closer to the objective lens from the focal position.

In the above-described microarray analyzing method, the microarray is a DNA microarray.

A fluorescence reading device receives, from a substrate, on which a concave and convex shape is formed and a plurality of probes that are able to bond to samples that are each fluorescence-labelled are arranged, light including fluorescence of the fluorescent label, and acquires image data based on the received light. The fluorescence reading device includes: a light source that emits illumination light including at least excitation light of a predetermined wavelength; an objective lens through which the illumination light is emitted to the substrate and which receives light from a surface of the substrate irradiated with the illumination light; an image acquiring unit that detects the light received by the objective lens, and acquires fluorescence image data according to the detected fluorescence, and substrate image data according to the light from the substrate; a detecting unit that detects, based on the substrate image data acquired by the image acquiring unit, a height difference of the concave and convex shape; a correcting unit that corrects, based on the height difference of the concave and convex shape detected by the detecting unit, the fluorescence image data; a holding means that holds the substrate; and a drive unit that moves the holding means along an optical axis of the objective lens. The drive unit moves the holding means such that the substrate is arranged at a position close to the objective lens with respect to a focal position of the objective lens when the substrate image data are acquired by the image acquiring unit.

The drive unit moves the holding means to arrange the substrate at a position corresponding to "α" that is set such that "α/f" is in a predetermined range, where "f" is a focal length of the objective lens and "α" is a distance by which the substrate is brought closer to the objective lens from the focal position.

By acquiring an image, from which a height difference of a substrate is accurately detectable, an alignment process is able to be properly performed and analysis is able to be performed, even for analysis of a DNA chip not arranged with a positive control or analysis of a chip having a small amount of DNAs contained in a sample.

BRIEF DESCRIPTION OF THE DRAWINGS

FIG. 4-1 is a schematic diagram illustrating a configuration of main parts of the optical system of the scanner according to an example.

FIG. 4-2 is a schematic diagram illustrating a configuration of main parts of the optical system of the scanner according to an example.

FIG. 5-1 is a diagram for explaining an image of the DNA chip read by the scanner according to an example.

FIG. 5-2 is a diagram explaining the image of the DNA chip read by the scanner according to an example.

FIG. 5-3 is a diagram explaining the image of the DNA chip read by the scanner according to an example.

FIG. 8 is a schematic diagram illustrating an image of the DNA chip read by the scanner according to an example.

FIG. 9-1 is a diagram explaining an image of the DNA chip read by the scanner according to an example.

FIG. 9-2 is a diagram explaining an image of the DNA chip read by the scanner according to an example.

FIG. 9-3 is a diagram explaining an image of the DNA chip read by the scanner according to an example.

FIG. 11-1B is a graph of light intensity change in the DNA chip according to the working example.

FIG. 11-2A is a diagram illustrating an image of the DNA chip according to the working example.

FIG. 11-2B is a graph of light intensity change in the DNA chip according to the working example.

FIG. 11-3A is a diagram illustrating an image of the DNA chip according to the working example.

FIG. 11-3B is a graph of light intensity change in the DNA chip according to the working example.

FIG. 11-4A is a diagram illustrating an image of the DNA chip according to the working example.

FIG. 11-4B is a graph of light intensity change in the DNA chip according to the working example.

FIG. 11-5A is a diagram illustrating an image of the DNA chip according to the working example.

FIG. 11-5B is a graph of light intensity change in the DNA chip according to the working example.

FIG. 11-6A is a diagram illustrating an image of the DNA chip according to the working example.

FIG. 11-6B is a graph of light intensity change in the DNA chip according to the working example.

FIG. 11-7A is a diagram illustrating an image of the DNA chip according to the working example.

FIG. 11-7B is a graph of light intensity change in the DNA chip according to the working example.

FIG. 11-8A is a diagram illustrating an image of the DNA chip according to the working example.

FIG. 11-8B is a graph of light intensity change in the DNA chip according to the working example.

FIG. 11-9A is a diagram illustrating an image of the DNA chip according to the working example.

FIG. 11-9B is a graph of light intensity change in the DNA chip according to the working example.

FIG. 11-10A is a diagram illustrating an image of the DNA chip according to the working example.

FIG. 11-10B is a graph of light intensity change in the DNA chip according to the working example.

FIG. 11-11A is a diagram illustrating an image of the DNA chip according to the working example.

FIG. 11-11B is a graph of light intensity change in the DNA chip according to the working example.

FIG. 11-12A is a diagram illustrating an image of the DNA chip according to the working example.

FIG. 11-12B is a graph of light intensity change in the DNA chip according to the working example.

FIG. 12-1 is a diagram illustrating an image of a slide glass according to a working example.

FIG. 12-2 is a graph illustrating light intensity change along an arrow between $P_{13}$ and $P_{13}'$ in the image of FIG. 12-1.

FIG. 12-3 is a graph illustrating a height difference on the slide glass along the arrow between $P_{13}$ and $P_{13}'$ in the image of FIG. 12-1.

Figure 1:
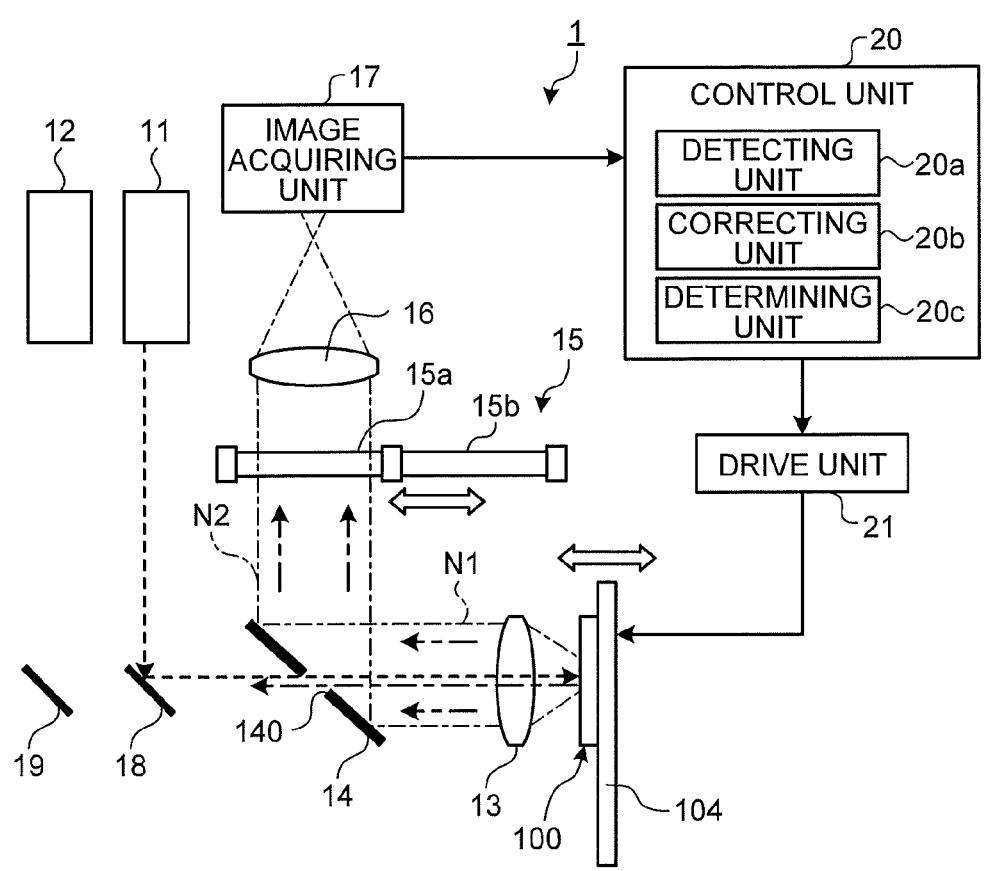
FIG. 1 is a schematic diagram illustrating an example of an optical system of a scanner according to an example.

REFERENCE SIGNS LIST 1, 2 Scanner
11, 12 Laser light source
13 Objective lens
14 Perforated mirror
14a Small mirror
15 Cut filter
15a, 15b Excitation light cut filter 16 Imaging lens
17 Image acquiring unit
18, 19 Mirror
20 Control unit
20a Detecting unit
20b Correcting unit
20c Determining unit
21 Drive unit
100 DNA chip
101 Block
102 Spot
103 Concave portion
104 Holding unit
140 Hole

DETAILED DESCRIPTION

Hereinafter, modes of carrying out our methods will be described in detail. This disclosure is not limited by the following examples. Further, each drawing referred to in the following description schematically illustrates shapes, sizes, and positional relations merely to an extent that allows contents of this disclosure to be understood. Therefore, our methods are not limited only to the shapes, sizes, and positional relations exemplified in each drawing.

In general, a fluorescence reading device (scanner) for microarrays one dimensionally or two dimensionally scans a light beam of an excitation wavelength and/or a microarray, detects fluorescence from a specimen on a substrate, generates an image from those data, and finds, based on that image, an intensity of fluorescence from each probe (a fluorescent label labelled on a sample). A preferable optical system of a scanner is illustrated in FIG. 1. FIG. 1 is a schematic diagram illustrating an example of the optical system of the scanner.

For example, a scanner 1 illustrated in FIG. 1 is configured of a laser light source, an objective optical system, an optical filter, an image acquiring unit that acquires fluorescence image data and alignment image data (substrate image data), and the like, and the scanner 1 has: a scanning mechanism (not illustrated, and a longitudinal direction of a substrate being referred to as y-axis and a direction orthogonal to the longitudinal direction being referred to as x-axis in a principal plane of the DNA chip 100 in this specification) to scan the above described DNA chip 100 (microarray) in two directions; and an automatic loader mechanism (not illustrated) on which a plurality of the DNA chips 100 are to be mounted.

Specifically, the scanner 1 includes: laser light sources 11 and 12 that each emit illumination light including at least excitation light of a specific wavelength to a substrate surface; an objective lens 13 that makes fluorescence from probes that have received the excitation light into parallel light; a perforated mirror 14 that is formed with a hole 140 through which the illumination light, which is emitted from each of the laser light sources 11 and 12 and which travels on an optical path N1, is passed towards the objective lens 13, the perforated mirror 14 bending at least a part of light emitted from the DNA chip 100 towards the optical path N2; a cut filter 15 having an excitation light cut filter 15a, which cuts light of a wavelength corresponding to the excitation light emitted from the laser light source 11 and lets only light of a wavelength corresponding to fluorescence from the sample that has hybridized to DNA probes to penetrate therethrough, and an excitation light cut filter 15b, which cuts light of a wavelength corresponding to the excitation light emitted from the laser light source 12 and lets only light of a wavelength corresponding to fluorescence from the sample that has hybridized to DNA probes to penetrate therethrough; an imaging lens 169 that forms an image of the fluorescence from the sample that has hybridized to the DNA probes; and an image acquiring unit 17 that acquires fluorescence image data by receiving the fluorescence from the sample that has hybridized to the DNA probes, receives reflected light from the substrate surface, and acquires, from intensity of that received light, alignment image data, from which a concave and convex shape of a surface of the block 101 of the DNA chip 100 is detectable. The excitation light cut filters 15a and 15b (cut filter 15) are freely insertably and removably provided with respect to the optical path N2 joining the perforated mirror 14 and image acquiring unit 17.

A hole 140 that causes the excitation light to be incident on the DNA chip 100 (objective lens 13) is normally provided in the center of the perforated mirror 14. Further, the hole 140 of the perforated mirror 14 has, as illustrated in FIG. 1, a function of geometrically separating the fluorescence or reflected light of the excitation light (detected light) from regularly reflected light from the substrate such that the regularly reflected light from the substrate, the regularly reflected light becoming a noise, is not guided towards the image acquiring unit 17 upon optical reading.

In the mode illustrated in FIG. 1, to downsize the device, the excitation light from the laser light sources 11 and 12 is refracted by mirrors 18 and 19 such that the excitation light is caused to reach the DNA chip 100.

Further, reference axes of the scanning mechanism are preferably orthogonal to each other to acquire an image with no strain. As the scanning mechanism, sliders are preferably used for both of the two axes, in general.

Furthermore, in this example, a control unit 20, which performs control of the whole scanner 1, and a drive unit 21, which performs control to move a holding unit 104 (holding means) that holds the DNA chip 100, such that a principal plane of the DNA chip 100 (block 101) follows the optical path N1 parallel to an optical axis of the objective lens 13, are included. Under the control of the drive unit 21, the DNA chip 100 approaches the objective lens 13 or separates from the objective lens 13.

Moreover, the control unit 20 has: a detecting unit 20a that detects a difference (hereinafter, referred to as "height difference") in height of the concave and convex shape on the surface of the DNA chip 100; a correcting unit 20b that corrects, based on the height difference detected by the detecting unit 20a, an image acquired by the image acquiring unit 17; and a determining unit 20c that determines a position of the spot 102 of the DNA chip 100 by referring to an analysis definition file recorded beforehand, based on the image corrected by the correcting unit 20b.

In this example, since the device is configured to add two types of fluorescent marks to the sample and to perform reading thereof, the laser light sources 11 and 12 and the excitation light cut filters 15a and 15b are included, the laser light sources 11 and 12 emitting light of wavelengths corresponding to the two types of fluorescent marks, and the excitation light cut filters 15a and 15b corresponding respectively to the wavelengths of the emitted excitation light. However, the device may be configured to add only one type of fluorescent mark to the sample and to perform reading thereof, or the device may be configured to add three or more types of fluorescent marks and to perform reading thereof. In any case, laser light sources and excitation light cut filters, which correspond to fluorescent marks (fluorescent dyes) to be used, just need to be provided.

Next, a method of acquiring fluorescence image data with the scanner 1 will be described. First, by using FIG. 1, the method of acquiring the fluorescence image data will be described. Hereinafter, although a mode in which Cy5 and Cy3 are used as the fluorescent dyes will be described, any one of the fluorescent dyes that label the sample may be used and limitation is not made thereto. For example, Fluorescein, FITC, Alexa Fluor 555, Rhodamine, Cy3.5, Texas Red, TAMRA, Oyster 650, Cy5.5, and the like may be used as the fluorescent dyes.

For example, the laser light source 11 for Cy5 (a laser light source that emits light of a wavelength of 635 nm, for example) emits laser light (that is, excitation light for the fluorescent dye Cy5) to read the fluorescent dye Cy5 first. The laser light is emitted to the DNA chip 100 via the perforated mirror 14 and the objective lens 13. Fluorescence from the fluorescent molecules that emit light by excitation with the emitted laser light and the laser light reflected and/or scattered by the chip surface are made into light beams approximately parallel to each other by the objective lens 13 and travels in a direction indicated with arrows in the figure on the optical path N1.

Thereafter, the fluorescence and the laser light are reflected by the perforated mirror 14, travel on the optical path N2, and become incident on the excitation light cut filter 15a for Cy5, which is arranged on the optical path N2. The laser light that has been regularly reflected by the surface of the DNA chip 100 passes through the hole 140 of the perforated mirror 14. The fluorescence from the fluorescent molecules that emit light by excitation penetrates through the excitation light cut filter 15a and is collected by the imaging lens 16.

On the contrary, the excitation light (light reflected and/or scattered by the chip surface) that has reached the excitation light cut filter 15a is cut off. The fluorescence collected by the imaging lens 16 becomes incident on the image acquiring unit 17. The image acquiring unit 17 subjects the received optical data to a photoelectric conversion process and outputs an electric signal (analog signal) according to intensity of the light. These steps are repeated while the DNA chip 100 is scanned in the two directions, and A/D conversion is performed on the electric signal output from the image acquiring unit 17 to generate the fluorescence image data.

Subsequently, the fluorescent dye Cy3 is read. Reading of the fluorescent dye Cy3 is performed similarly to the reading of the fluorescent dye Cy5, except that the laser light source 11 for Cy5 is replaced by the laser light source 12 for Cy3 (for example, a laser light source that emits light of a laser wavelength of 532 nm) and the excitation light cut filter 15a for Cy5 is replaced by the excitation light cut filter 15b for Cy3. That is, the laser light source 12 for Cy3 emits the laser light (that is, excitation light for the fluorescent dye Cy3) and the excitation light cut filter 15b for Cy3 removes the excitation light (that is, light reflected and/or scattered by the chip surface) that has reached the excitation light cut filter 15b to generate the fluorescence image data similarly to the case of the fluorescent dye Cy5.

Figure 2:
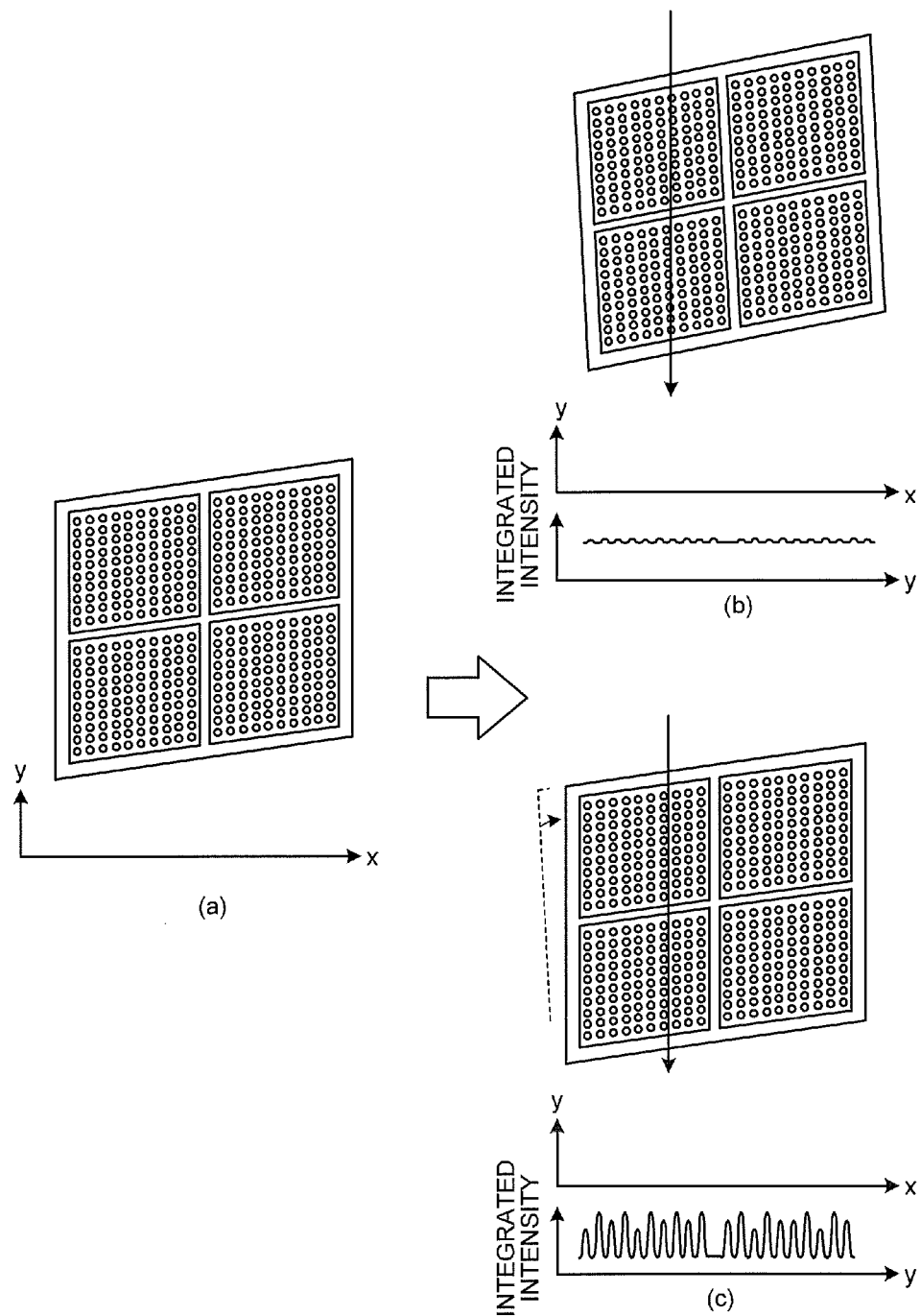
FIG. 2 is a diagram schematically illustrating an example of an image of a DNA chip read by the scanner.

FIG. 2 is a diagram schematically illustrating an example of an image of the DNA chip 100 read by the scanner 1. If the scanning mechanism of the scanner includes two sliders, the sliders are not necessarily orthogonal to each other. They may be deviated from each other, at the time of assembling the device, over time, or the like. Therefore, the image of the DNA chip 100 read by the scanner 1 is possibly inclined with respect to the x-axis as illustrated in FIG. 2(*a*), for example. When the scanning directions of the scanning mechanism in the acquired image are not consistent with the x-axis and/or the y-axis like that, the acquired fluorescence image data become strained and the detection areas of the template are unable to be positioned correctly with respect to the acquired image. Further, even if the x-axis and y-axis of the sliders are mechanically orthogonal to each other, since the x-axis and y-axis of the fluorescence image are not orthogonal to the axes of the sliders, the DNA chip 100 may be rotated when the DNA chip 100 is set and as a result, the fluorescence image may be rotated. In this case also, the detection areas of the template are unable to be positioned correctly with respect to the acquired image.

Therefore, preferably, the deviation in the orthogonality is detected from the image and corrected to obtain an image equivalent to the image acquired by the scanning mechanism in which the sliders are orthogonal to each other. More specifically, the fluorescence image data are projected in the y-axis direction with respect to the x-axis to calculate an integrated intensity (integrated value of each pixel value) for each coordinate X. This process is repeated while rotating the fluorescence image data about the origin of coordinates by a preset angle. For example, an integrated intensity graph when the projecting direction and the array direction of the spots in the y-axis direction are deviated becomes a graph with small amplitude as illustrated in FIG. 2(*b*).

On the contrary, an integrated intensity graph when the projecting direction and the array direction of the spots in the y-axis direction coincide with each other becomes a graph in which the amplitude changes at certain intervals and the signal amplitude becomes maximum, as illustrated in FIG. 2(*c*). By using such characteristics of the projected data, an angle at which a standard deviation of the integrated intensity takes a maximum value is found to detect an array angle of the spots 102 with respect to the y-axis. Similarly, by finding an array angle with respect to the x-axis and performing image processing such as shear deformation, the array directions of the spots are able to be made orthogonal to each other.

When the fluorescence image data are acquired as described above, if the amount of the specimen is very small, since the number of DNA probes (the DNA probes that have hybridized to the DNA sample) that emit fluorescence is reduced for both of the fluorescent dyes Cy5 and Cy3, the boundary between blocks is not recognized, and since the orthogonality of the image is unable to be corrected, the alignment process becomes impossible.

Figure 3:
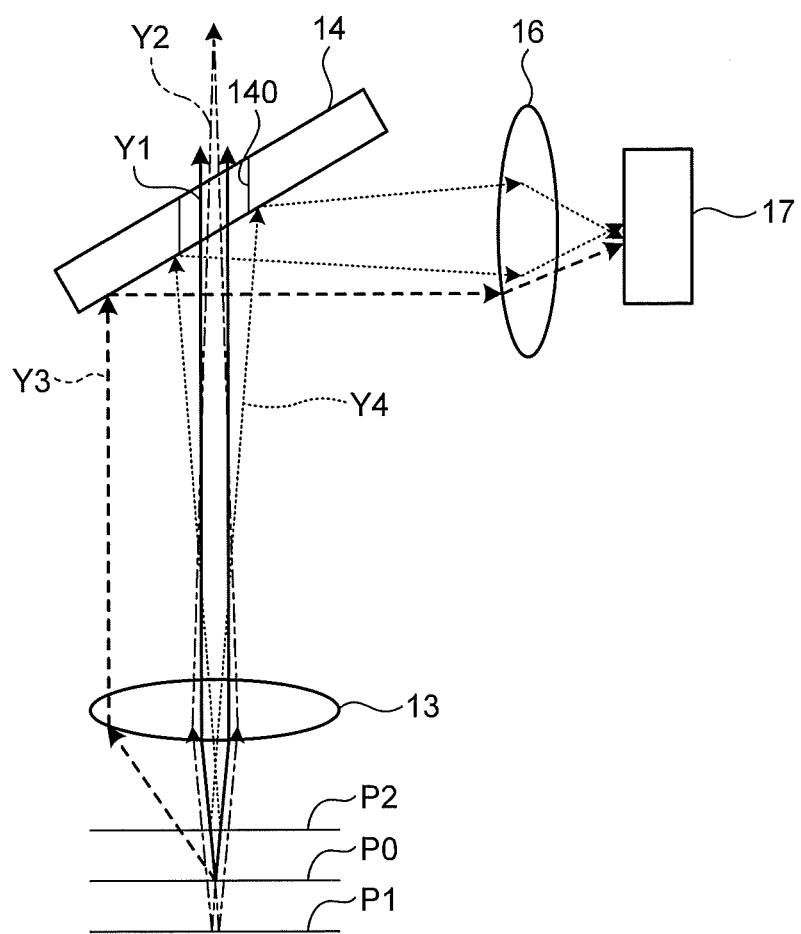
FIG. 3 is a schematic diagram illustrating a configuration of main parts of the optical system of the scanner according to an example.
Figures 1, 4:
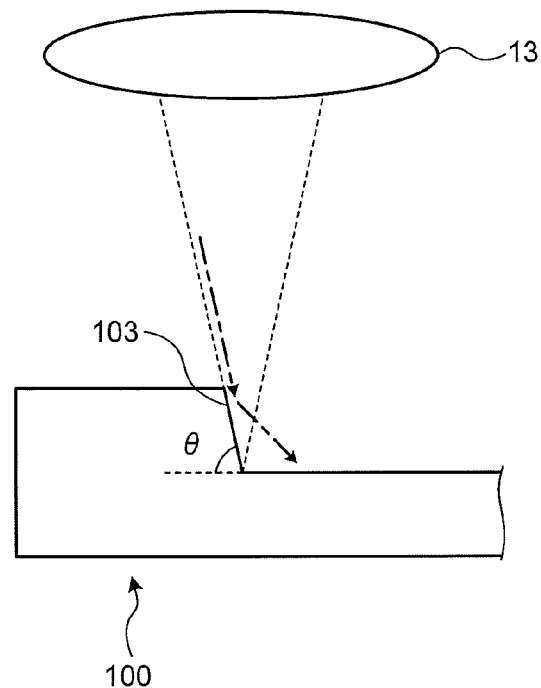
Figures 2, 4:
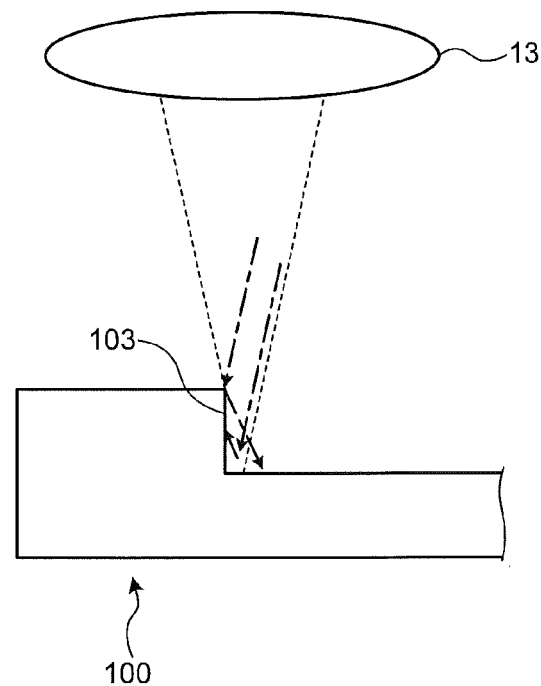

Therefore, in addition to the above-mentioned fluorescence image data, alignment image data are also acquired without resetting the DNA chip 100. When the alignment image data are acquired, preferably, the DNA chip 100 is arranged closer to the objective lens 13, than the focal position at which the laser light has been collected by the objective lens 13 is and the alignment image data are acquired. FIG. 3 is a schematic diagram illustrating a configuration of main parts of the optical system of the scanner 1. FIG. 4-1 and FIG. 4-2 are schematic diagrams illustrating configurations of the main units of the optical system of the scanner 1 according to the example, FIG. 4-1 being a diagram illustrating a case where the concave portion 103 of the DNA chip 100 has a slope, and FIG. 4-2 being a diagram illustrating when the concave portion 103 of the DNA chip 100 does not have a slope.

FIG. 3 illustrates how incident light is incident, through the perforated mirror 14, on a surface (light irradiation surface) of the block 101 of the DNA chip 100. The incident light is parallel light represented by laser light. If the surface of the block 101 is assumed to be at a focal position (the just-focused position, or a surface position P0) at which the incident light has been collected by the objective lens 13, the regularly reflected light therefrom is collected by the objective lens 13, the diameter of the regularly reflected light ideally becomes the same as that of the incident light, and most of the regularly reflected light passes through the hole 140 of the perforated mirror 14 and mostly not guided towards the image acquiring unit 17 (solid lined arrows Y1 in FIG. 3). However, by aberration (spherical aberration, coma aberration, astigmatism, or the like) of the objective lens 13, some of the reflected light is reflected by the perforated mirror 14 and guided to the image acquiring unit 17, but an intensity thereof is small.

On the contrary, if the surface of the block 101 of the DNA chip 100 is at a position (a surface position P1) farther than the focal position, regularly reflected light from that surface, as viewed from the objective lens 13, is regarded as a point light source emitted from a portion farther than the focal position (surface position P0). Therefore, that reflected light is focused on the incident light side of the objective lens (dashed-dotted lined arrow Y2 in FIG. 3). Thus, at the position of the perforated mirror 14, the diameter of light becomes smaller than the diameter of the light from the surface at the surface position P0. Accordingly, since most of the regularly reflected light passes through the hole 140 of the perforated mirror 14, without being guided to the image acquiring unit 17 side, it becomes even darker.

For such reasons, when the reflected light from the DNA chip 100 is imaged, for example, an image, in which the top surface (a portion close to the objective lens) of the block 101 is bright and the bottom portion (a portion far from the objective lens) of the concave portion 103 is dark, is able to be acquired.

However, if the surface of the DNA chip 100 has small scratches or adhered matter, diffused reflection occurs there. An optical path of that diffused reflection is illustrated with a broken lined arrow Y3 in FIG. 3. This diffused light is reflected by the perforated mirror 14 and advances towards the image acquiring unit 17. Therefore, if the surface of the DNA chip 100 has small scratches or adhered matter, artifacts due to the diffused reflection occur and an image of concaves and convexes of the substrate may not be able to be made. In particular, if the substrate is made of resin, the substrate is often manufactured by molding using metal molds, and cut traces on the metal molds made by the working tool are transferred directly onto the substrate and artifacts due to diffused reflection often occur.

To solve the above problem, the alignment image data are acquired at the position (surface position P2) where the surface to be imaged of the DNA chip 100 has been brought closer to the objective lens 13 than the focal position (surface position P0) is. As a result, as illustrated with dotted lined arrows Y4 in FIG. 3, the regularly reflected light is regarded as the point light source that performs emission from a portion closer than the focal length as viewed from the objective lens 13, and thus the regularly reflected light is diffused even after passing the objective lens 13 and is reflected towards the image acquiring unit 17 by the perforated mirror 14. Thus, influence by the diffused light (for example, the broken lined arrows Y3) is lessened and only stepped (edge) portions of the substrate are darkened.

The surface position P2 of the surface to be imaged is preferably set by using a relation "α/f" between a focal length "f" of the objective lens 13 and a distance "α" by which the DNA chip 100 is brought closer from the focal position (surface P0) to the objective lens 13. A range of this "α/f" is preferably 0.017 to 0.17, and more preferably 0.033 to 0.17. The drive unit 21 performs, under control by the control unit 20, control to move the holding unit 104 such that the surface to be imaged of the DNA chip 100 is arranged at the set position at "α".

As illustrated in FIG. 4-1, if a side surface of the concave portion 103 of the DNA chip 100 is sloped at an angle θ, light reflected therefrom is directed to a different direction. Further, if the side surface of the concave portion 103 vertically (angle θ=90 degrees) rises (FIG. 4-2), the reflected light returning to the lens is light that has been reflected twice. If reflected twice, the light becomes very weak (normally, since a reflectivity of a transparent body is about 4%, a light intensity of the two-time reflection is ¹⁄₂₅ of the intensity of one-time reflection). Therefore, the stepped portions of the substrate become dark.

Figure 14:
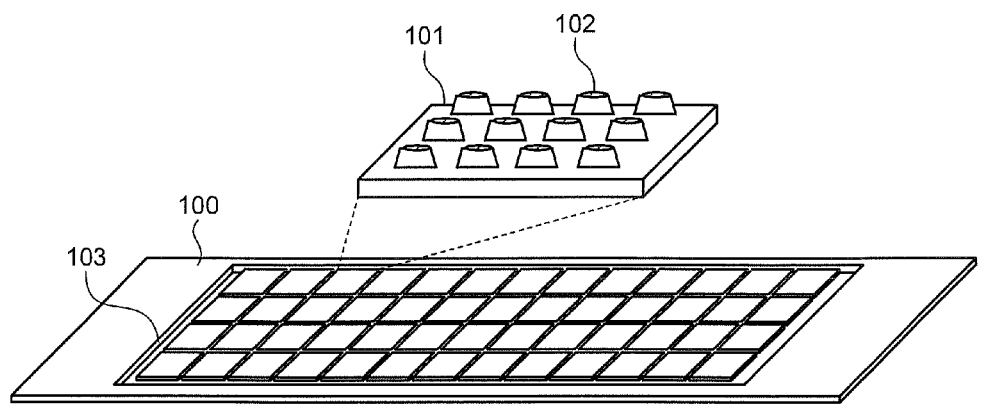
FIG. 14 is a diagram illustrating an example of a DNA chip used in a conventional DNA chip analysis.

A preferable range of the angle θ of the concave portion 103 is 20 degrees to 90 degrees. If this angle is greater than 90 degrees, the substrate becomes difficult to be made and if the angle is less than 20 degrees, the stepped portions may be unable to be recognized in the image data. The DNA chip 100 as illustrated in FIG. 14 is preferably manufactured by injection molding of resin in terms of productivity. In that case, in terms of ease of molding (ease of removal from the metal molds), the angle θ is more preferably 20 degrees to 80 degrees.

Figures 1, 5:
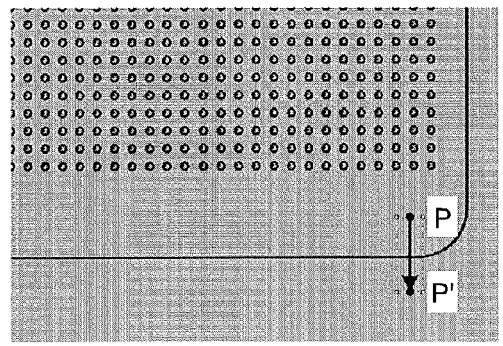
Figures 2, 5:
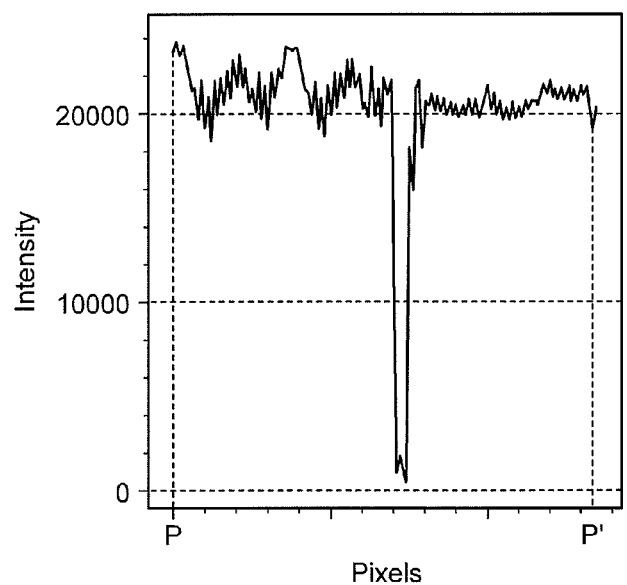
Figures 3, 5:
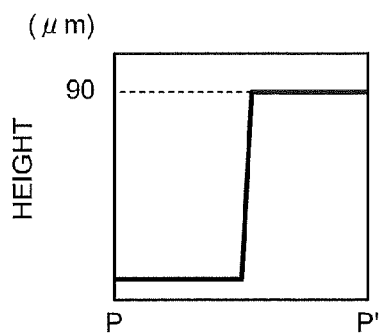

An example of an alignment image acquired as described above is illustrated in FIG. 5-1 to FIG. 5-3. FIG. 5-1 to FIG. 5-3 are diagrams explaining an image of a microarray read by the scanner according to the example. FIG. 5-1 is a diagram illustrating the alignment image. FIG. 5-2 is a graph illustrating light intensity change along an arrow between P and P' in the alignment image of FIG. 5-1. FIG. 5-3 is a graph illustrating a height difference of the DNA chip 100 along the arrow between P and P' in the alignment image of FIG. 5-1. From FIG. 5-2, it can be confirmed that the reflected light intensity has been reduced at the position corresponding to the side surface of the concave portion 103 of the DNA chip 100 and an image of the concave and convex shape on the substrate has been able to be made. The position of the concave portion 103 of the DNA chip 100 in the alignment image is able to be determined based on this and the fluorescence image is able to be aligned.

A light source usable in acquiring the alignment image data is preferably a laser light source (for example, wavelengths of 405 nm, 532 nm, and 635 nm). For a laser light source, since the light is parallel, due to the phenomena described with reference to FIG. 3, edges (light intensity differences) are clearly detectable in the alignment image data.

Specifically, to acquire the alignment image data with the above described device configuration, it is preferable to emit laser light from the laser light source 11 for Cy5 and to use the excitation light cut filter 15b for Cy3. In general, a band pass filter that penetrates 550 nm to 600 nm is generally used for the excitation light cut filter 15b for Cy3 in many cases, but since light (635 nm) at the wavelength of the excitation light for Cy5 penetrates slightly through the excitation light cut filter 15b in general (for example, an OD value of light at 635 nm is approximately "5"), an image of the concave and convex shape of the DNA chip 100 is able to be made as illustrated in FIG. 5-1. That is, instead of fluorescence from fluorescent molecules that emit light by excitation with light of a particular wavelength, the reflected light and/or the scattered light from the substrate surface is received to make an image of the concave and convex shape of the substrate itself When the alignment image data are acquired, the DNA chip 100 is preferably arranged at a place closer to the objective lens 13 than the focal position is. The focal position is able to be found by measuring intensities of fluorescence from the respective DNA probes while fixing the height of the objective lens 13 and moving the DNA chip 100 in the height direction (optical axis direction of the objective lens 13) and actually measuring the height at which the values of the intensities of fluorescence become the largest. On the contrary, the height of the DNA chip 100 may be fixed and the height of the objective lens 13 may be changed. When the reflected light and/or scattered light at the surface of the DNA chip 100 is received, based on the above mentioned relation, "α/f", the position of the surface (surface to be imaged) of the DNA chip 100 is preferably brought closer to the lens by a distance equal to or greater than 100 μm from the focal position. More preferably, this distance is equal to or greater than 200 μm. The upper limit of this approached distance is not particularly limited as long as the DNA chip 100 does not collide with the objective lens 13, but for a device like the scanner 1, the upper limit is normally equal to or less than 3000 μm. Although a light source that emits excitation light for exciting the fluorescent molecules is preferably used as the light source for acquiring the alignment image data to reduce the number of parts of the scanner, a light source that acquires the alignment image data may be additionally provided.

Further, a method of not using a filter when the alignment image data are acquired may be adopted. However, if a filter is not used since a light intensity incident on the image acquiring unit becomes too large, the light detecting mechanism of the image acquiring unit may be damaged. Accordingly, when the laser light source 11 for Cy5 emits the laser light, a filter through which the emitted wavelength of the light source slightly penetrates is preferably used, for example, the excitation light cut filter 15b is used as described above. On the contrary, the laser light source 12 for Cy3 may emit the laser light and the excitation light cut filter 15a may be used. Alternatively, an ND filter may be used instead of the excitation light cut filters 15a and 15b, or the output of the laser light itself may be made weaker to obtain the alignment image data without using the excitation light cut filters 15a and 15b or the ND filter. Of course, a combination of these may be adopted.

In FIG. 5-1 to FIG. 5-3, acquiring was performed by bringing the substrate (DNA chip 100) closer to the lens by 250 μm from the focal point. As described above, by actively bringing the substrate from the focal point closer to the lens and actively receiving the reflected light of the laser light, the alignment image data, in which the edge shape of the substrate surface is expressed as illustrated in FIG. 5-1, are acquired.

Figure 6:
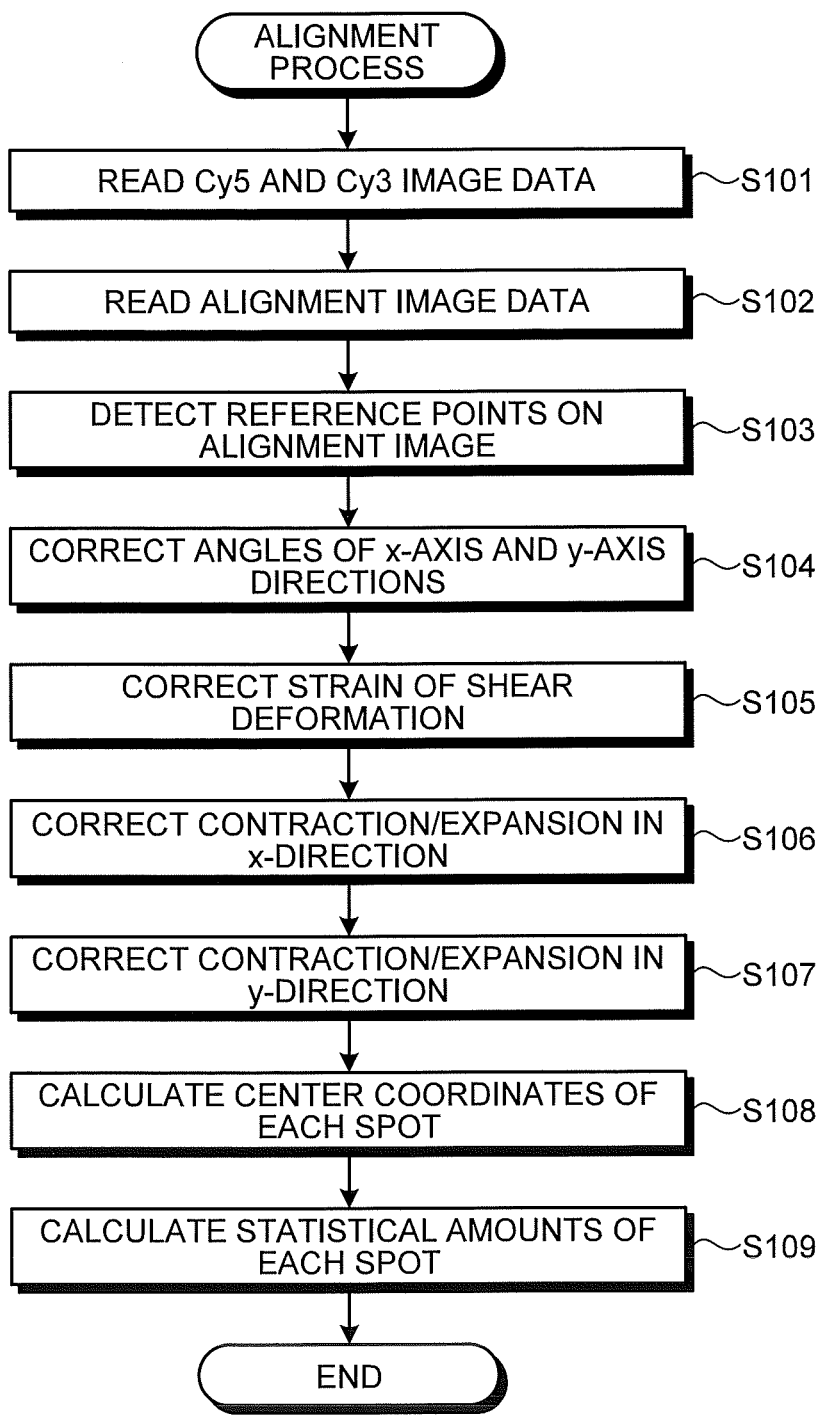
FIG. 6 is a flow chart illustrating an alignment process for an image according to an example.

By using the alignment image data acquired as described above, edges (outer edges of the concave portion 103) of the substrate are accurately detectable. Hereinafter, an example of specific procedure of alignment including the above method when the DNA chip 100 is used will be described. FIG. 6 is a flow chart illustrating an alignment process for an image according to the example.

First, the DNA chip 100 is set in the scanner 1, and fluorescence image data of the fluorescent dyes Cy5 and Cy3 are read by the image acquiring unit 17 as described above (Step S101). Subsequently, laser light is emitted from the laser light source 11 for Cy5 and the excitation light cut filter 15b for Cy3 is used to read the alignment image data by the image acquiring unit 17 while the DNA chip 100 is kept set (Step S102). When this is done, the DNA chip 100 is, as described above, arranged at a position closer to the objective lens 13 than the focal position is. At Step S102, laser light may be emitted from the laser light source 12 for Cy3 and the excitation light cut filter 15a for Cy5 may be used.

At and after Step S103, the positions of the respective DNA probes in the fluorescence image data are determined by using the alignment image data and analysis is performed.

Figure 7:
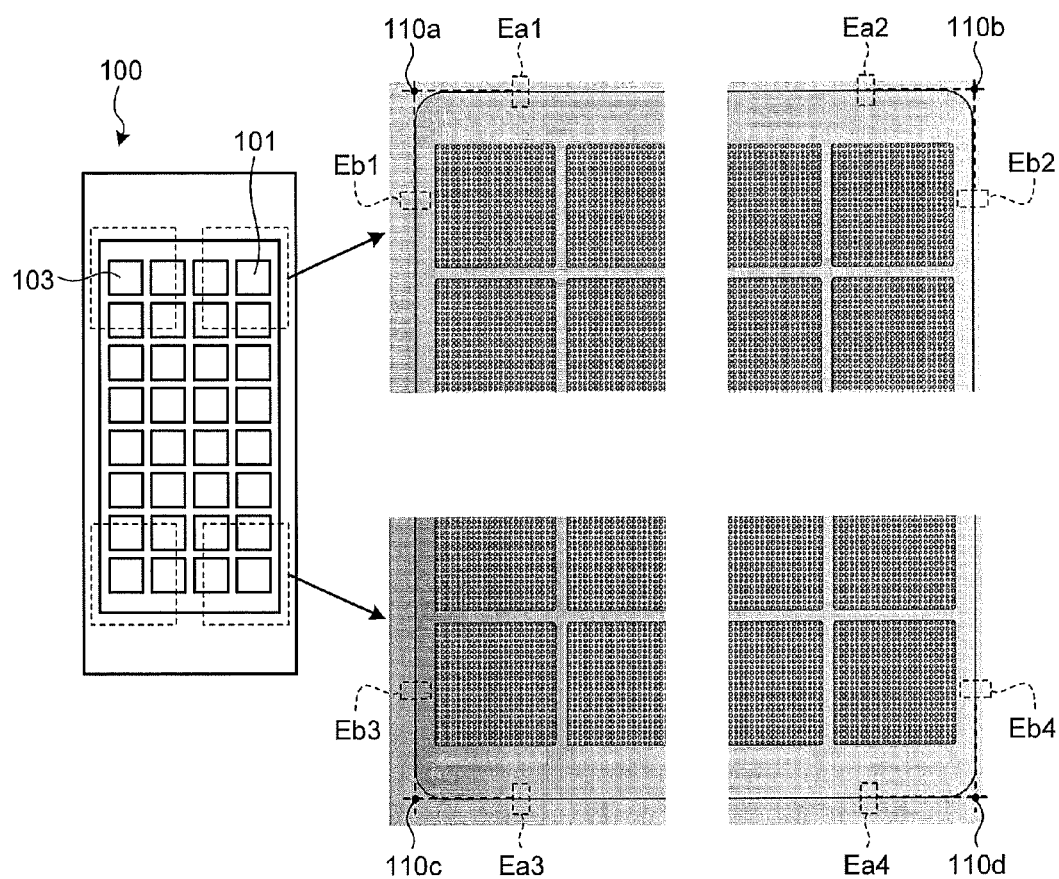
FIG. 7 is a schematic diagram explaining a method of detecting the coordinates of four corners of alignment image data according to an example.

Specifically, first, at least three reference points in the alignment image data are detected (Step S103). The at least three reference points may be coordinates of four corners in the alignment image, as illustrated in FIG. 7, for example. A method of detecting the coordinates of the four corners is executed by the detecting unit 20a, and may be the above described determination of the position of the concave portion 103 by the edge detection using lightness and darkness information.

As illustrated in FIG. 7, on the DNA chip 100, areas Ea1 to Ea4 and Eb1 to Eb4, from which the outer edges of the concave portion 103 are possibly detected by the detecting unit 20a, are set beforehand, and in each of these areas, change in light intensity along the arrow between P and P' as illustrated in FIG. 5-1 is measured to detect a height difference of the DNA chip 100. Thereafter, by using the central positions of the height differences detected in the respective areas Ea1 to Ea4 and Eb1 to Eb4, the detecting unit 20a linearly joins the central position of the area Ea1 with the central position of the area Ea2 to obtain one side of the outer edges of the concave portion 103. As to the other three sides of the outer edges of the concave portion 103, the central position of the area Ea3 and the central position of the area Ea4, the central position of the Eb1 and the central position of the area Eb2, and the central position of the area Eb3 and the central position of the area Eb4 are each linearly joined to each other. Thereby, the outer edges of the concave portion 103 in the alignment image acquired by the image acquiring unit 17 are formed. Further, by finding the intersection points (coordinates) between the straight lines respectively formed by the joining, the four corners of the concave portion 103 are able to be acquired as reference points 110a to 110d.

Subsequently, at Steps S104 and S105, strain of the fluorescence image data is corrected based on the reference points.

Specifically, the correcting unit 20b detects an inclination angle θx with respect to the x-axis and an inclination angle θy with respect to the y-axis, of each side of the outer edges of the concave portion 103, from the coordinates of the above-mentioned four reference points 110a to 110d, for example (Step S104). The inclination angles θx and θy each desirably take an average value of angles of two line segments in the corresponding (opposite) directions among four line segments joining the coordinates of the four corners. Even if the number of reference points is three, the inclination angles θx and θy are able to be calculated. As illustrated in FIG. 8(a) and FIG. 8(b), the correcting unit 20b rotates the fluorescence image data by using the inclination angle θy of the side (side of the outer edges of the concave portion 103) corresponding to the y-axis with respect to the y-axis as a correction angle so that the side of the concave portion 103 corresponding to the y-axis is made parallel to the y-axis. Further, as illustrated in FIG. 8(b) and FIG. 8(c), the correcting unit 20b rotates the fluorescence image data by using the inclination angle θx of the side (side of the outer edges of the concave portion 103) corresponding to the x-axis with respect to the x-axis as a correction angle, so that the side of the concave portion 103 corresponding to the x-axis is made parallel to the x-axis. After the conversion, as illustrated in FIG. 8(c), an image with outer edges respectively parallel with the x-axis and y-axis is able to be acquired.

Further, the correcting unit 20b executes, based on the above described inclination angles θx and θy and the following Equations (1) and (2), for the spots 102 arrayed regularly in the two directions that have been detected as described above, conversion (shear deformation) on the rotated image (Step S105). Thereby, strain of the shear deformation in the image is corrected. In the following Equation (1), "(x, y)" corresponds to coordinates before conversion and "(X, Y)" corresponds to coordinates after conversion. Further, θxy corresponding to the deviation (orthogonality of the reference axes of the scanning mechanism) in the scanning mechanism of the scanner is found by subtracting the inclination angle θy from the inclination angle θx as expressed by the following Equations (1) and (2)

$$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix} \quad (1)$$

$$\theta xy = \theta x - \theta y. \quad (2)$$

Further, if the DNA chip 100 is a resin molded article, the resin may expand due to moisture absorption and temperature change in the hybridization step and the washing step. Although this depends also on the processing time in each of the steps, the resin may expand by several tens of μm to influence the accuracy of alignment.

Therefore, the correcting unit 20b calculates the chip lengths in the x-axis direction and y-axis direction from the above-mentioned coordinates of the four corners, for example, and performs contraction-expansion correction on the fluorescence image data to achieve consistency with designed values (Steps S106 and S107).

Figures 1, 9:
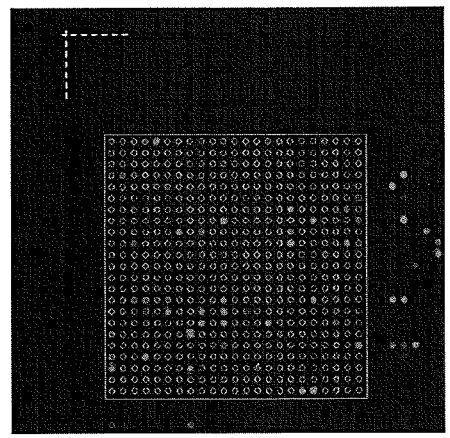
Figures 2, 9:
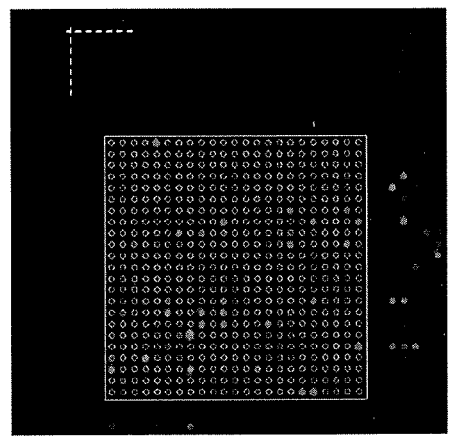
Figures 3, 9:
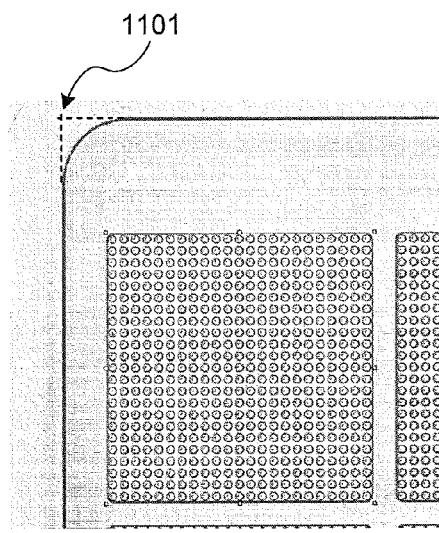
Figure 15:
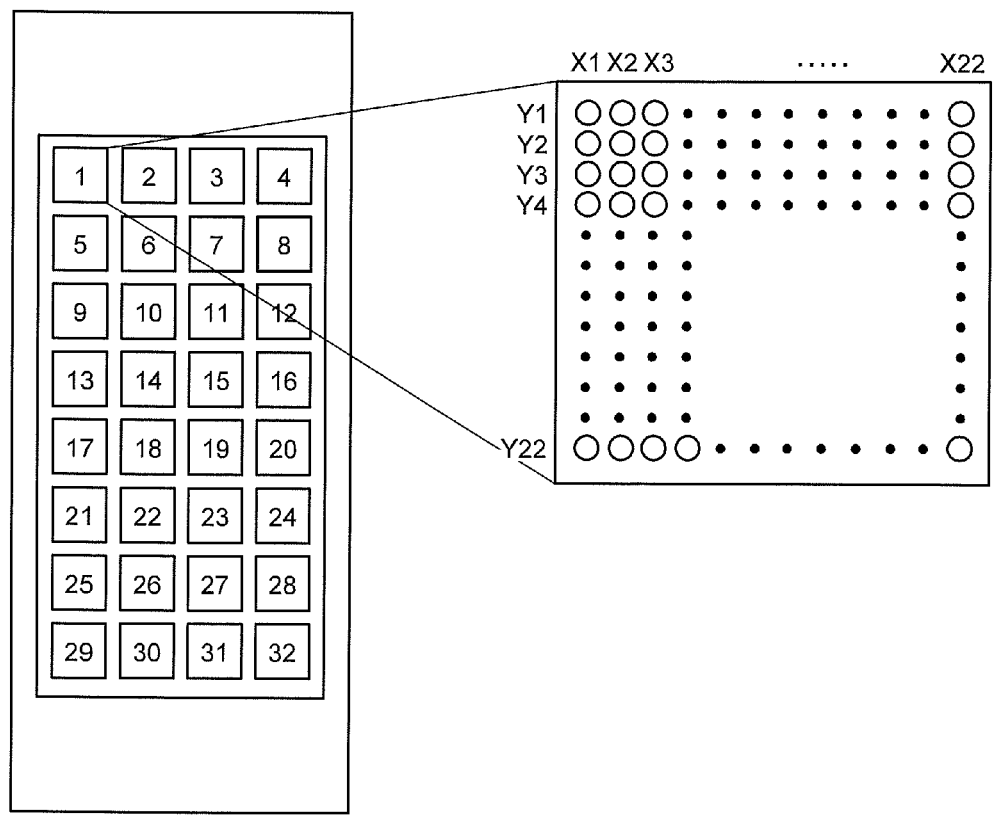
FIG. 15 is a schematic diagram illustrating an example of a template applied to fluorescence image data of a conventional DNA chip.

Subsequently, with respect to the fluorescence image data that have been subjected to the angle correction, shear deformation correction, and contraction-expansion correction by the correcting unit 20b as described above, the determining unit 20c performs alignment of the fluorescence image by referring to the analysis definition file. The positional information of each spot in the template that has been stored in the analysis definition file beforehand is center coordinates of that spot with an upper left corner (reference point 110a) of the chip being a point of origin, for example. With respect to the image that has been subjected to the contraction correction in Step S107, the determining unit 20c determines a position of each spot (probe) by calculating each spot frame with the coordinates of the upper left corner being the point of origin, for example, and performs alignment as illustrated in FIG. 9-1 to FIG. 9-3 (Step S108). FIG. 9-1 is an image illustrating a result of the alignment performed on the fluorescence image data of Cy3 and FIG. 9-2 is an image illustrating a result of the alignment performed on the fluorescence image data of Cy5. Thereby, each spot 102 is able to be associated with the detection area by being assigned with a template (see FIG. 15) corresponding to the respective spots 102. Further, FIG. 9-3 illustrates, as an example, a result of the alignment performed on the alignment image data for confirmation. As illustrated in FIG. 9-3, it is understood that by the alignment process, the straight lined portions at one corner of the outer edges of the concave portion 103 of the DNA chip 100 are orthogonal to each other at the reference point 1101.

Thereafter, statistical amounts such as average values, median values, and standard deviations, for the signal intensities of pixels within the spot radius are calculated from the center coordinates of the respective spots that have been found in Step S108, and the various types of numerical data, together with block numbers to which the spots belong, matrix numbers of the spots, and names of the arranged DNA probes, are output as a file (Step S109). By the above described process, the strain or the like is corrected and accurate statistical amounts, such as average values, median values, and standard deviations, are calculated, with respect to the acquired fluorescence image data.

The order of the above-mentioned Steps S101 and S102 and the order of the Steps S106 and S107 may be changed.

The fluorescence image data acquired based on the hybridization of the DNA sample to the DNA probes are processed in the above manner to acquire desired numerical data, but the acquired various types of numerical data are used for analyzing presence of the gene to be sought for, whether or not a certain gene has been expressed, or the degree of the expression, and so on.

Further, in analysis of the DNA chip 100 as described above, correction and alignment of an image are performed by using the concaves and convexes formed on the DNA chip 100. Thus, a process of positioning the detection areas arranged on the DNA chip 100 becomes accurately executable even for an image with a small amount of DNAs included in the sample extracted from the specimen and with less DNA probes emitting light, as well as for an image acquired by a reading device with bad accuracy in the scanning mechanism.

According to the above described example, since the alignment image data are acquired at the position (surface position P2) where the surface of the DNA chip 100 to be imaged has been brought closer to the objective lens 13 from the focal position (surface position P0), an image, from which a height difference of the substrate is accurately detectable, is able to be acquired. Thereby, an alignment process is able to be performed properly and analysis is enabled, even for analysis of a DNA chip in which a positive control is not arranged and for analysis of a chip having a small amount of DNAs in the sample.

Figure 10:
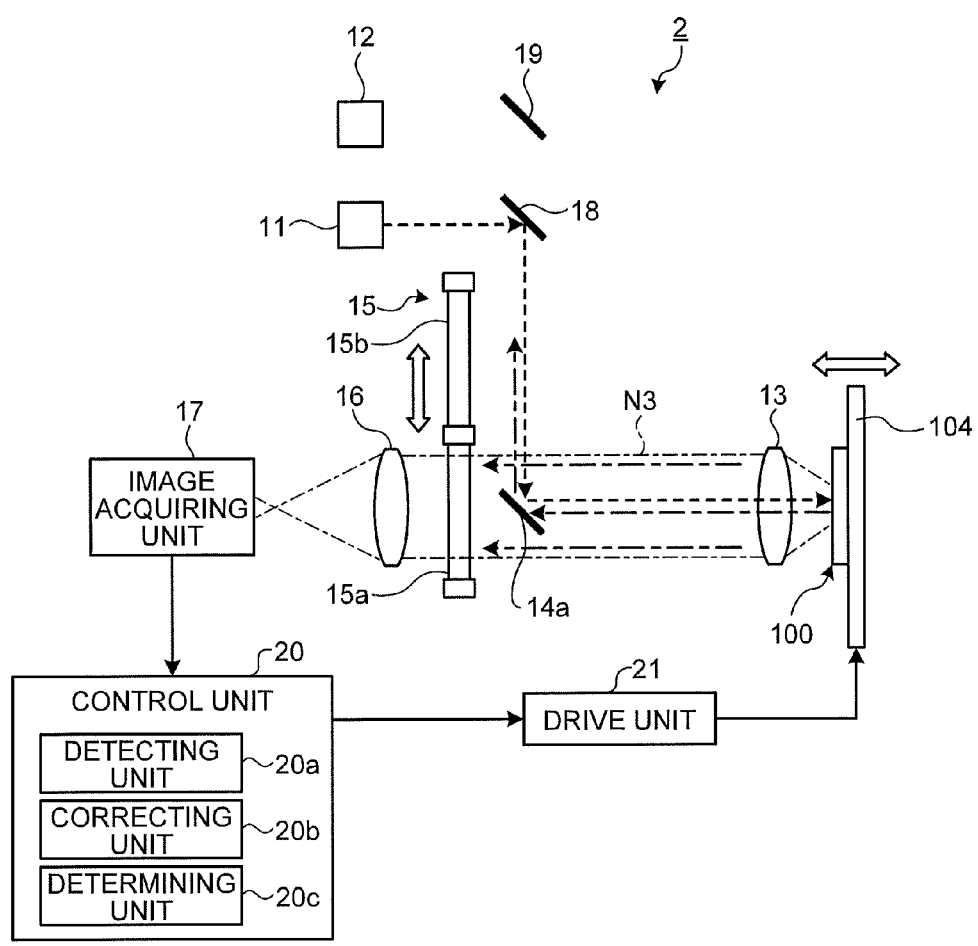
FIG. 10 is a schematic diagram illustrating another example of the optical system of the scanner according to an example.

FIG. 10 illustrates another mode of the optical system suitable for the scanner. In FIG. 10, to structural elements that are the same as those of the scanner 1 illustrated in FIG. 1, the same signs are appended. To cause excitation light to be reflected by a small mirror 14a and be incident on the DNA chip 100 and not to guide, upon optical reading, regularly reflected light from the DNA chip 100, the regularly reflected light becoming a noise, towards the image acquiring unit 17, a scanner 2 illustrated in FIG. 10 has, by using a small mirror 14a instead of the perforated mirror 14 of the scanner 1, a function of geometrically separating the fluorescence or reflected light (detected light) of the excitation light from the regularly reflected light. Thereby, the regularly reflected light is able to be separated from an optical path N3. With this configuration, the same effects as those of the above described scanner 1 are able to be obtained.

In the above described example, although the example of the DNA chip with the DNA probes spotted on the substrate has been described, our methods are also applicable to a chip on which RNAs, proteins, small specimens, low-molecular compounds, cells, or the like have been spotted.

For example, the same method may be used even when proteins (antibodies) instead of DNA probes are immobilized onto the DNA chip 100 having the concave and convex shape as described above and presence or absence of reaction with a specimen and quantification are detected with fluorescence. There are cases when proteins present in a sample cell lysate are labeled with Cy5, proteins present in a control cell lysate are labeled with Cy3, and these are mixed to react with an antibody array, and a method where proteins are labeled with biotin instead of the fluorescence, they are bonded to an antibody array, and thereafter, a signal is sensitized by using enzyme-labeled avidin. Even in these cases, our methods, accurate alignment is enabled and various types of numerical data of fluorescence intensities are able to be output as files. For an RNA array also, this method is able to be used when hybridization between RNAs immobilized onto a substrate (spots 102) having a concave and convex shape and fluorescence-labeled DNAs or RNAs is detected with fluorescence. To small specimens and cell arrays, our methods are also applicable when bonding reaction between the small specimens or cells immobilized onto a substrate having a concave and convex shape and a fluorescence-labeled specimen (for example, antibody) is detected with fluorescence.

WORKING EXAMPLES

Hereinafter, our methods will be described with working examples, but this disclosure is not to be limited by these examples.

By ultra precision machining, a metal mold corresponding to a substrate having a shape like the DNA chip 100 illustrated in FIG. 14 was manufactured, and a substrate, as the DNA chip 100, made of polymethylmethacrylate (PMMA), was manufactured by using this metal mold through injection molding. The metal mold had cut traces made by the tool and thus, the substrate was in a state where the tool cut traces have been transferred thereon. The fluctuation in the substrate height due to the cut traces was actually measured to be equal to or less than 1 μm.

DNA probes were immobilized onto top surfaces of convex portions (spots 102) of the manufactured DNA chip 100, up to hybridization was performed, and a fluorescence image and an alignment image were acquired with a DNA chip scanner (3D-Gene (registered trademark) Scanner). The following (1) to (4) are the device configurations and conditions for the acquirement of the fluorescence image and alignment image.

(1) The optical system of the scanner 1 illustrated in FIG. 1 was used as the optical system of the scanner. That is, the optical scanner has the perforated mirror 14 for causing laser light to be incident on the DNA chip 100 and passing regularly reflected light therethrough from the substrate.

(2) When fluorescence was acquired from the spots 102, the height (the distance between the objective lens 13 and the DNA chip 100) of the DNA chip 100 was changed and the height position at which the fluorescence intensity became the strongest was regarded as "0". This position is the focal position (surface position P0) of the laser light. In this example, since a DNA sample labelled with Cy5 was used, laser at a wavelength of 635 nm and a band pass filter for Cy5 were used. The scanner has a function of being able to adjust the distance between the substrate and the lens.

(3) A laser (wavelength of 635 nm) that measures fluorescence of Cy5 was used, and a filter that is the same as the band pass filter, which is used when Cy3 is measured, was used. The OD value at 635 nm is about "5" for the Cy3 filter used in this working example, and the Cy3 filter slightly lets the wavelength of 635 nm penetrate therethrough. By adopting the above described combination for the combination of the laser light and filter, reflected and/or scattered light from the substrate surface is able to be acquired and made into image data.

(4) An offset position (the distance from the focal position to the substrate surface) was changed from −500 μm to +1500 μm, and images of the reflected and/or scattered light were compared (FIG. 3). The expression, "the offset position is zero" means that the substrate is at the focal position (surface position P0) of the laser light stopped down by the objective lens. Further, an offset position with a negative sign indicates that the substrate is at a position (surface position P1) far from the objective lens with reference to the focal position and an offset position with a positive sign indicates that the substrate is at a position (surface position P2) close to the objective lens with reference to the focal position.

Figures 1A, 11:
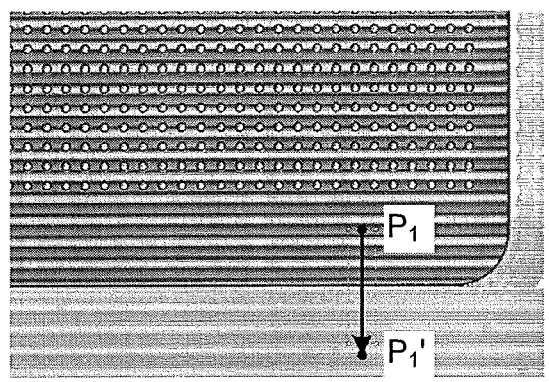
FIG. 11-1A is a diagram illustrating an image of a DNA chip according to a working example.
Figures 1B, 11:
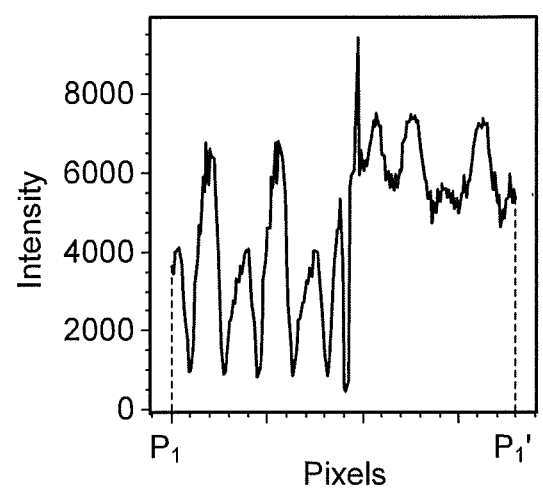
Figures 2A, 11:
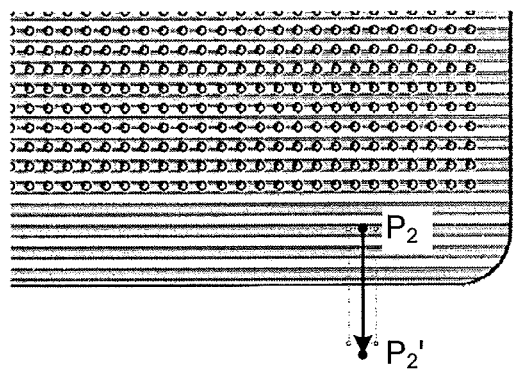
Figures 2B, 11:
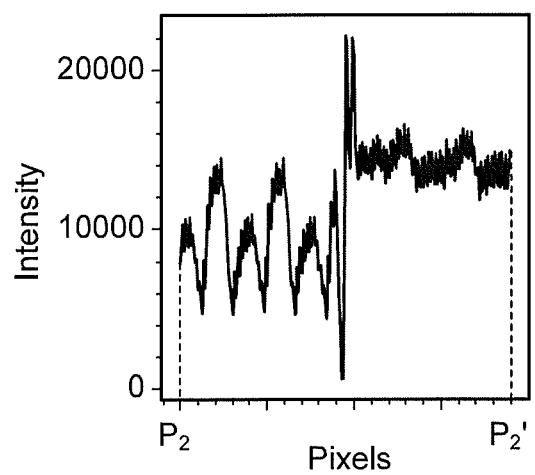
Figures 3A, 11:
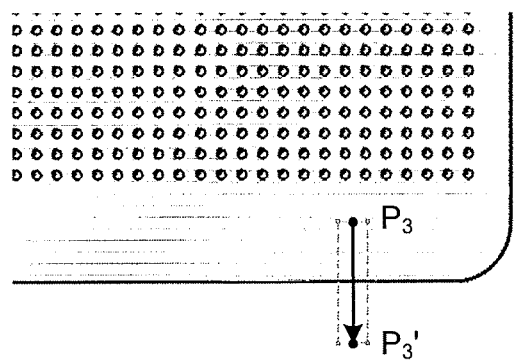
Figures 3B, 11:
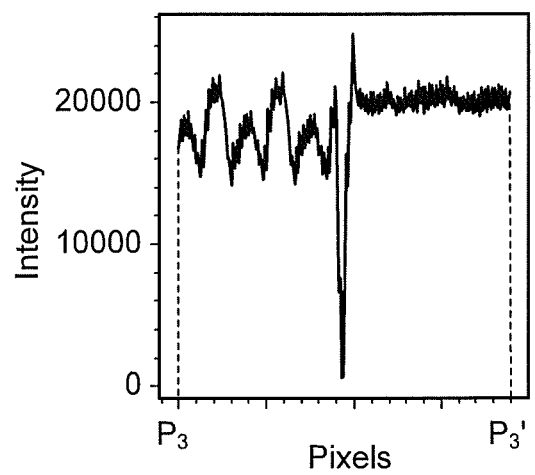
Figures 4A, 11:
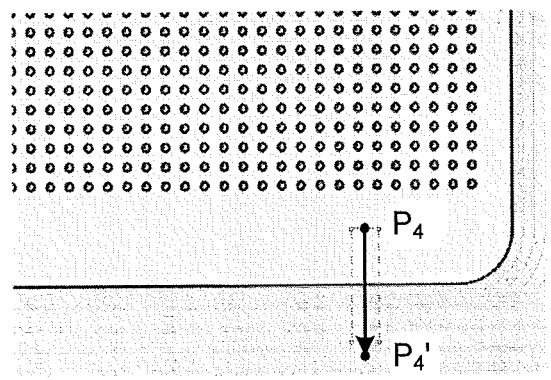
Figures 4B, 11:
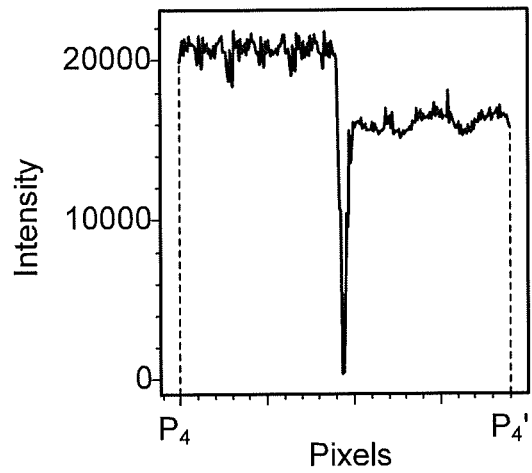
Figures 5A, 11:
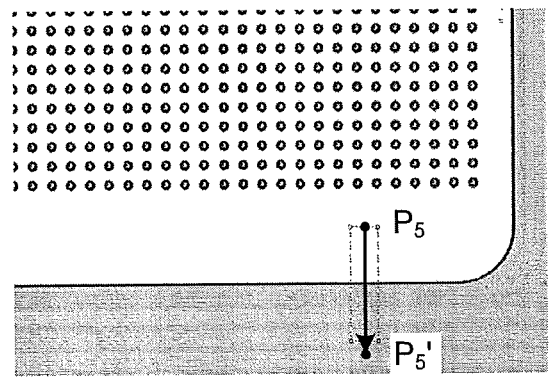
Figures 5B, 11:
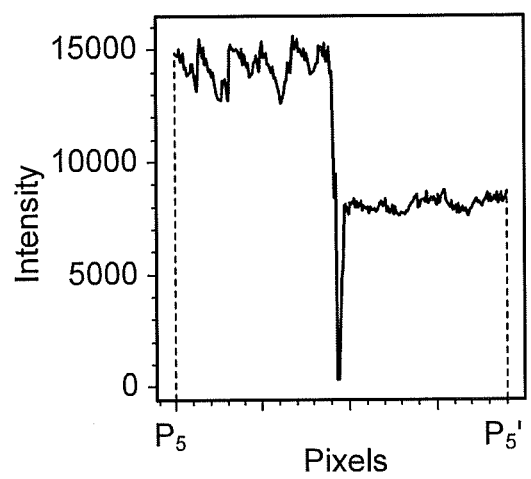
Figures 6A, 11:
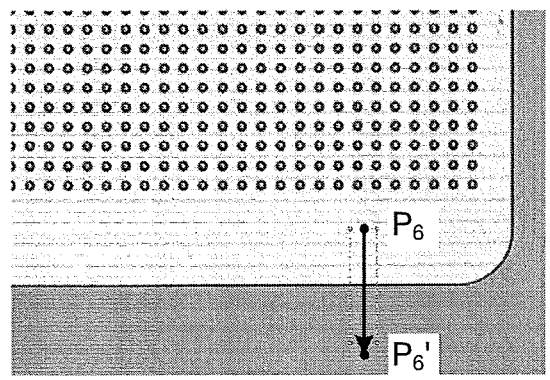
Figures 6B, 11:
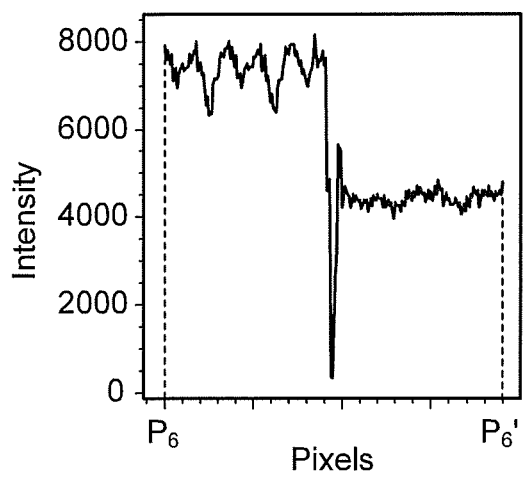
Figures 7A, 11:
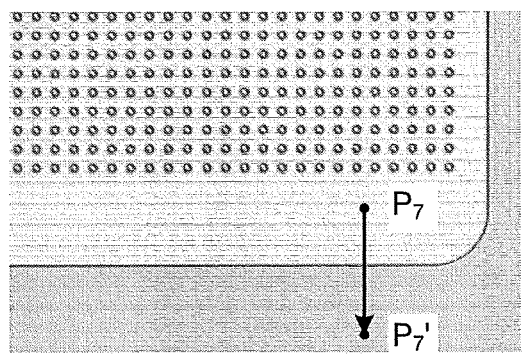
Figures 7B, 11:
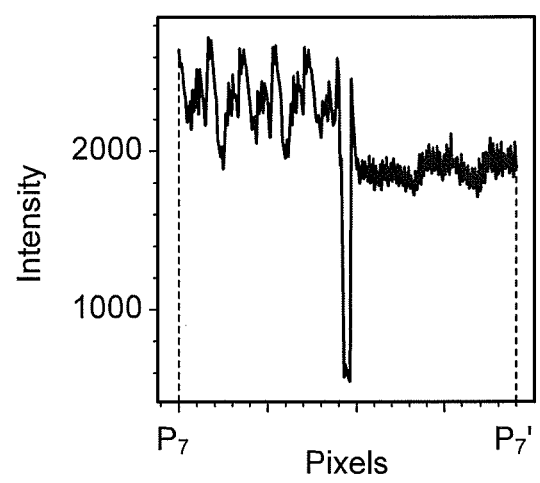
Figures 8A, 11:
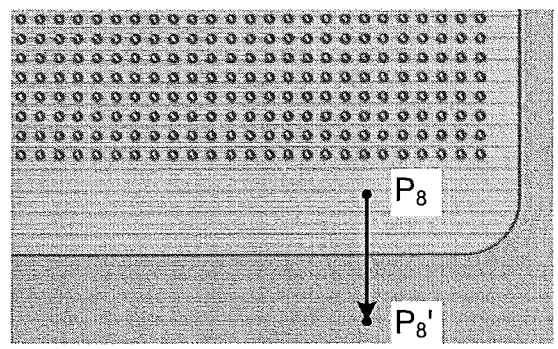
Figures 8B, 11:
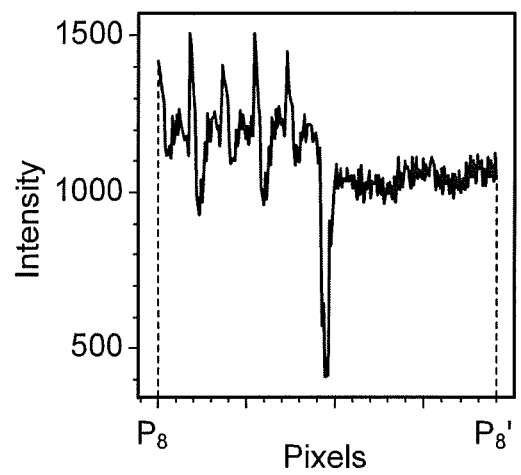
Figures 9A, 11:
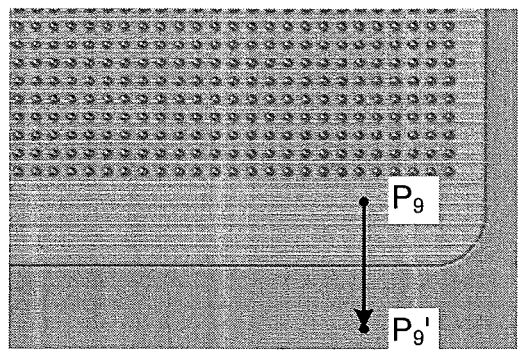
Figures 9B, 11:
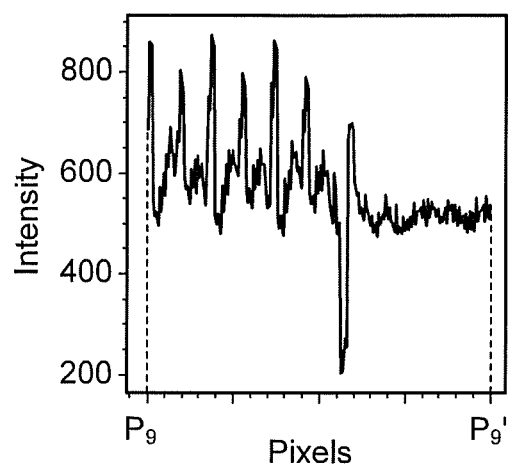
Figures 10A, 11:
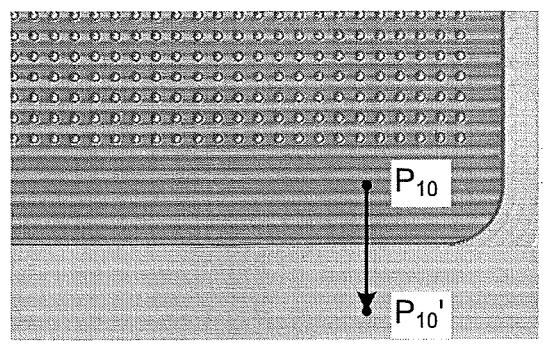
Figures 10B, 11:
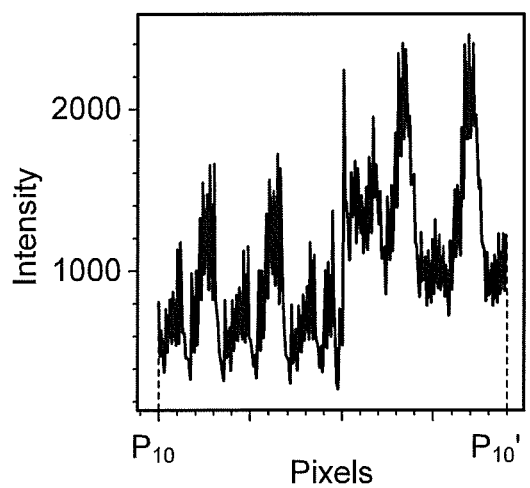
Figures 11, 11A:
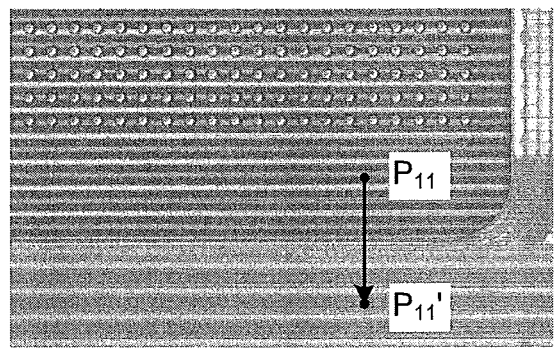
Figures 11, 11B:
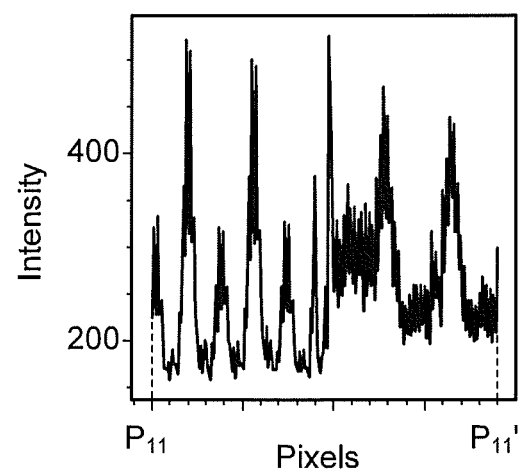
Figures 11, 12, 12A:
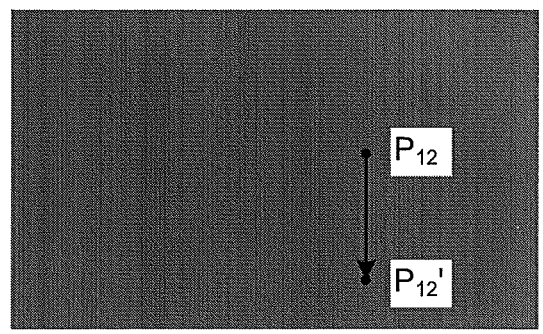
Figures 11, 12, 12B:
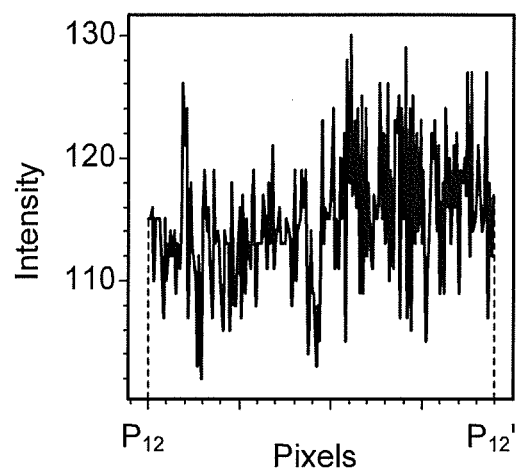
Figures 1, 12:
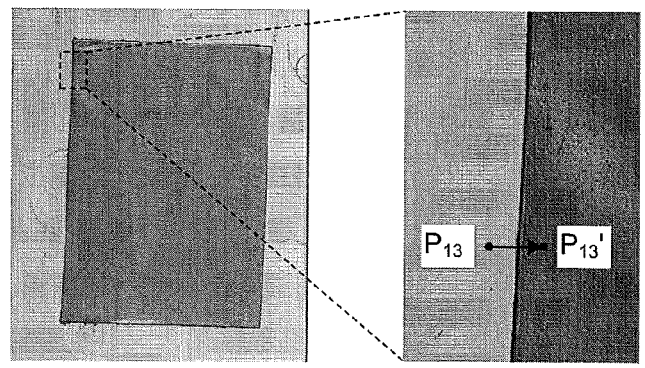
Figures 2, 12:
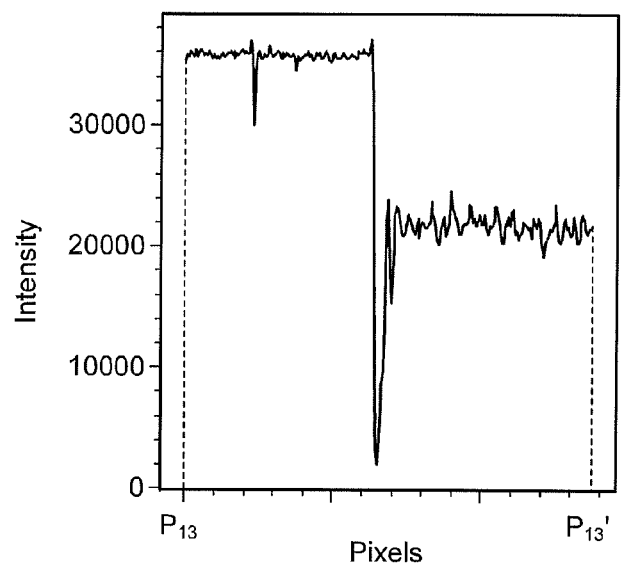
Figures 3, 12:
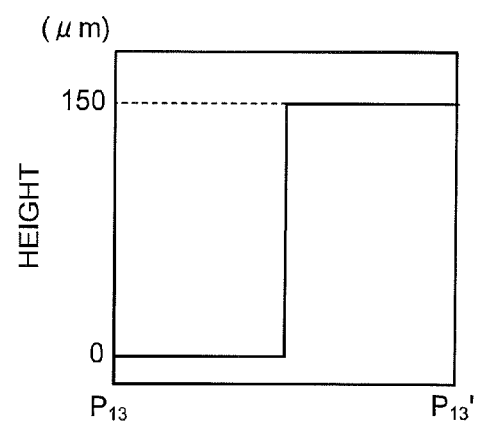
Figure 13:
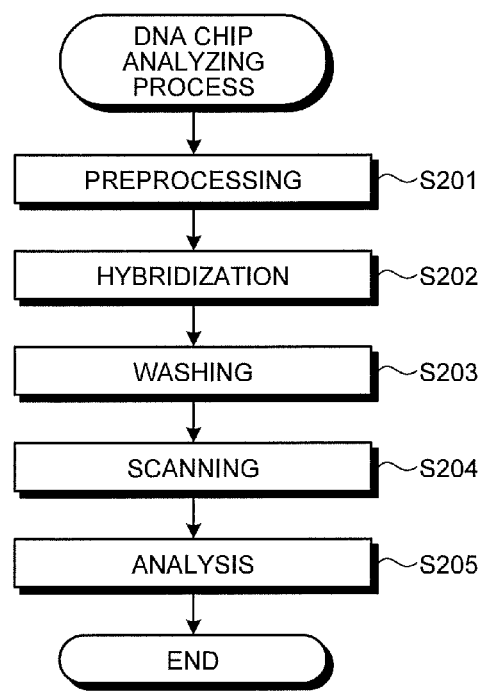
FIG. 13 is a flow chart illustrating details of a series of procedural steps of conventional DNA chip analysis.

FIG. 11 (FIG. 11-1 to FIG. 11-12) are images (A) of the DNA chip 100 (substrate) read by the scanner 1 according to the working example and graphs (B) of light intensity change. FIG. 11-1 is an image in a case where the offset position is "0" and a graph indicating light intensity change along the arrow between $P_1$ and $P_1'$ in the image. FIG. 11-2 to FIG. 11-9 are images for when the offset positions are +100, +200, +300, +400, +500, +750, +1000, and +1500, and graphs indicating the light intensity change along the arrow between $P_2$ and $P_2'$, arrow between $P_3$ and $P_3'$, arrow between $P_4$ and $P_4'$, arrow between $P_5$ and $P_5'$, arrow between $P_6$ and $P_6'$, arrow between $P_7$ and $P_7'$, arrow between $P_8$ and $P_8'$, and arrow between $P_9$ and $P_9'$, in the images. FIG. 11-10 to FIG. 11-12 are images for when the offset positions are −100, −200, and −500, and graphs indicating the light intensity change along the arrow between $P_{10}$ and $P_{10}'$, arrow between $P_{11}$ and $P_{11}'$, and arrow between $P_{12}$ and $P_{12}'$, in the images. The images illustrated in FIG. 11 are images corresponding to alignment image data corrected by the above described correcting unit 20b.

As illustrated in FIG. 11, when the offset position was equal to or greater than +200 μm, images and light intensity change graphs, which have clear contrast corresponding to edge portions of the substrate (the actual height difference being 90 μm, and the slope angle θ illustrated in FIG. 4-1 being 70 degrees), were acquired (FIG. 11-3A and FIG. 11-3B to FIG. 11-9A and FIG. 11-9B). On the contrary, when the offset position was 0 μm, due to the roughness (equal to or less than a height of 1 μm) of the substrate surface by the cut traces, diffused reflection occurred, and disorder in the reflection intensity consistent with the cut traces but inconsistent with the concave and convex shape of 90 μm occurred (FIG. 11-1B). When the offset position was +100 μm, as compared to 0 μm, although the influence of the cut traces is lessened, the influence still remained (FIG. 11-2B). Further, when the offset positions were −100 μm and −200 μm, diffused reflection occurred and disorder in the reflection intensity occurred (FIG. 11-10B and FIG. 11-11B) due to the roughness (equal to or less than a height of 1 μm) of the substrate surface caused by the cut traces. When the offset position was −500 μm, the image of the substrate surface was unable to be acquired (FIG. 11-12A).

As a result, when the offset position was equal to or greater than +200 μm and equal to or less than +1000 μm, particularly preferable images, in which the edge portions of the substrate were dark, were acquired. When the offset position was +1500 μm, although the edge portions were recognizable, the image as a whole tended to be dark. When the offset position was negative, only images, in which the edges were totally not recognizable, were able to be acquired.

Further, based on these results, the offset position upon acquisition of an alignment image was changed among −500 μm, 0 μm, +100 μm, +200 μm, +500 μm, +1000 μm, +1250 μm, and +1500 μm, to perform evaluation of whether an alignment process of an image was able to be performed properly, according to the following procedure (1)' to (5)'.

(1)' A total of twenty DNA chips that have been subjected to a hybridization process were prepared. The shape of the substrates of the DNA chips is as illustrated in FIG. 14. The height difference of the edge portions is 90 μm and the angle θ illustrated in FIG. 4-1 is 70 degrees.

(2)' For each of the DNA chips, a fluorescence image of Cy5 was acquired with the offset position being 0 μm (focal position).

(3)' Alignment images were acquired respectively at offset positions of −100 μm, 0 μm, +100 μm, +200 μm, +500 μm, +750 μm, +1000 μm, +1250 μm, and +1500 μm. When this was done, a laser (wavelength of 635 nm) that measures fluorescence of Cy5 was used, and a filter, which is the same as the band pass filter used when Cy3 is measured, was used.

(4)' Reference points corresponding to the reference points 110a to 110d in FIG. 7 were detected, based on the respective alignment image data, by an edge detecting method using lightness and darkness information.

(5)' For each of the twenty DNA chips, Steps S104 to S108 of FIG. 6 were performed to confirm whether the fluorescence images were correctly aligned at the positions where the offset positions were −100 μm, 0 μm, +100 μm, +200 μm, +500 μm, +1000 μm, +1250 μm, and +1500 μm. The results are illustrated in Table 1.

TABLE 1

| Offset position (μm) | Number of chips succeeded in alignment | Alignment success rate |
|---|---|---|
| −100 | 0 | 0% |
| 0 | 6 | 30% |
| +100 | 19 | 95% |
| +200 | 20 | 100% |
| +500 | 20 | 100% |
| +1000 | 20 | 100% |
| +1250 | 16 | 80% |
| +1500 | 14 | 70% |

From the above, it is understood that, when the alignment image is acquired, by bringing the DNA chip closer to the objective lens with respect to the focal position, reliability of the alignment clearly increases. It is understood that in the above working example, the reliability is largely increased by bringing the substrate closer to the objective lens by +200 μm from the focal position when the alignment image is acquired.

The f-value of the objective lens installed in the scanner 1 according to the working example was 6.0 mm. Therefore, from the above results, when the offset position (α) was in a range of +100 to +1000, the preferable range of "α/f" was in a range of 0.017 (100/6000) to 0.17 (1000/6000). In this range, the success rate is equal to or greater than 95%. More preferably, the offset position is in a range of +200 to +1000, and a range of "α/f" is from 0.033 (200/6000) to 0.17 (1000/6000). In this range, the alignment success rate is 100%.

REFERENCE EXAMPLE

A tape having a thickness of 150 μm was affixed onto a flat slide glass to be set in the above described scanner 1. In a state where the offset amount was +250 μm, a laser (wavelength of 635 nm) that measures fluorescence of Cy5 was used and a filter, which is the same as the band pass filter used when Cy3 is measured, was used, to acquire image data corresponding to an alignment image. This condition corresponds to the angle θ illustrated in FIG. 4-1 being 90 degrees. The results are illustrated in FIG. 12-1 to FIG. 12-3.

FIG. 12-1 to FIG. 12-3 are an image of the slide glass according to this reference example and a graph of fluorescence intensity. FIG. 12-1 is an image acquired by the scanner 1. FIG. 12-2 is a graph illustrating light intensity change along an arrow between $P_{13}$ and $P_{13}'$ in the image of FIG. 12-1. FIG. 12-3 is a graph illustrating a height difference on the slide glass along the arrow between $P_{13}$ and $P_{13}'$ in the image of FIG. 12-1. As a result, we found that even for a tape affixed to a slide glass, a height difference is able to be found from change in intensity of light. Since the portions corresponding to the edges are dark, it is considered that there is no problem even if the angle θ is 90 degrees.

INDUSTRIAL APPLICABILITY

A detecting method, a microarray analyzing method, and a fluorescence reading device are suitable to perform an alignment process properly by acquiring an image, from which a height difference of a substrate is accurately detectable.

The invention claimed is:

1. A detecting method comprising:
   irradiating a substrate having a concave and convex shape with laser light collected by a lens; and
   detecting a height difference of the concave and convex shape by acquiring light intensity of reflected light and/or scattered light from the substrate as image data, wherein
   a light irradiation surface of the substrate is arranged at a position 1) closer to the lens than a focal position of the lens is, and 2) corresponding to "α" set such that "α/f" is 0.017 to 0.17, where "f" is a focal length of the lens and "α" is a distance by which the substrate is brought closer to the lens from the focal position, and reflected light and/or scattered light from the light irradiation surface is received as detected light, and a height difference of the substrate is detected based on a change in intensity of the received light.

2. The detecting method according to claim 1, wherein an optical system that separates, from the detected light, regularly reflected light coming from the light irradiation surface, is used, at a time the light irradiation surface of the substrate is arranged at the focal position.

3. A microarray analyzing method of irradiating a microarray, on which a concave and convex shape is formed and a plurality of probes that are able to bond to samples that are each fluorescence-labeled are arranged, with light including an excitation wavelength for the fluorescent label, via an objective lens, receiving light from the microarray, and analyzing the microarray based on an image that is based on the received light, the microarray analyzing method comprising:
   a fluorescence image data acquiring step of acquiring fluorescence image data by detecting fluorescence from the fluorescent label;

an alignment image data acquiring step of acquiring, by detecting light from a surface of the microarray, alignment image data for performing alignment of the fluorescence image data;

a detecting step of detecting, based on a change in light intensity in the alignment image data, a height difference of the concave and convex shape;

a correcting step of correcting, based on the height difference of the concave and convex shape detected by the detecting step, the fluorescence image data; and a position determining step of determining a position of each probe in the fluorescence image data corrected by the correcting step, wherein in the alignment image data acquiring step, the alignment image data are acquired in a state where the surface of the microarray is arranged at a position 1) close to the objective lens with respect to a focal position of the objective lens, and 2) corresponding to "α" set such that "α/f" is 0.017 to 0.17, where "f" is a focal length of the objective lens and "α" is a distance by which the microarray is brought closer to the objective lens from the focal position.

4. The microarray analyzing method according to claim 3, wherein in the detecting step, from the alignment image data, three or more reference points are detected based on the change in light intensity, and in the correcting step, strain of the fluorescence image data is corrected based on the detected reference points.

5. The microarray analyzing method according to claim 4, wherein in the correcting step, inclination angles θx and θy of the alignment image data based on the reference points are acquired, and strain of shear deformation of the fluorescence image data is corrected based on the inclination angles θx and θy and Equations (1) and (2) below $$\begin{pmatrix} X \\ Y \end{pmatrix} = \begin{pmatrix} 1 & 0 \\ -\tan\theta xy & 1 \end{pmatrix} \begin{pmatrix} x \\ y \end{pmatrix} \quad (1)$$

$$\theta xy = \theta x - \theta y. \quad (2)$$

6. The microarray analyzing method according to claim 3, wherein the microarray is a DNA microarray.

7. The microarray analyzing method according to claim 4, wherein the microarray is a DNA microarray.

8. The microarray analyzing method according to claim 5, wherein the microarray is a DNA microarray.

9. A fluorescence reading device that receives, from a substrate, on which a concave and convex shape is formed and a plurality of probes able to bond to samples that are each fluorescence-labeled are arranged, light including fluorescence of the fluorescent label, and acquires image data based on the received light, the fluorescence reading device comprising:

a light source that emits illumination light including at least excitation light of a predetermined wavelength;

an objective lens through which the illumination light is emitted to the substrate and which receives light from a surface of the substrate irradiated with the illumination light;

a light detector and converter that receives reflected light and fluorescence from the objective lens, and produces fluorescence image data according to the detected fluorescence and substrate image data according to the reflected light from the substrate;

a calculator that determines, based on the substrate image data acquired by the image acquiring unit, a height difference of the concave and convex shape;

a corrective calculator that corrects, based on the height difference of the concave and convex shape determined by the calculator, the fluorescence image data;

a holder that holds the substrate; and a driver that moves the holder along an optical axis of the objective lens, wherein the driver moves the holder such that the substrate is arranged at a position 1) close to the objective lens with respect to a focal position of the objective lens when the substrate image data are acquired by the detector, and 2) corresponding to "α" set such that "α/f" is 0.017 to 0.17, where "f" is a focal length of the lens and "α" is a distance by which the substrate is brought closer to the lens from the focal position.

* * * * *

UNITED STATES PATENT AND TRADEMARK OFFICE
CERTIFICATE OF CORRECTION

Page 1 of 1

PATENT NO. : 9,823,197 B2
APPLICATION NO. : 14/433972
DATED : November 21, 2017
INVENTOR(S) : Nagino et al.

It is certified that error appears in the above-identified patent and that said Letters Patent is hereby corrected as shown below:

In the Specification

In Column 8
At Line 3, please change "169" to --16--.

Signed and Sealed this
Eighth Day of May, 2018

Andrei Iancu
*Director of the United States Patent and Trademark Office*